US006864255B2

(12) United States Patent
Geuns-Meyer et al.

(10) Patent No.: US 6,864,255 B2
(45) Date of Patent: Mar. 8, 2005

(54) SUBSTITUTED TRIAZINYL AMIDE DERIVATIVES AND METHODS OF USE

(75) Inventors: Stephanie D. Geuns-Meyer, Medford, MA (US); Lucian V. DiPietro, Gloucester, MA (US); Joseph L. Kim, Wayland, MA (US); Vinod F. Patel, Acton, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 10/120,939

(22) Filed: Apr. 10, 2002

(65) Prior Publication Data

US 2003/0087908 A1 May 8, 2003

Related U.S. Application Data

(60) Provisional application No. 60/282,977, filed on Apr. 11, 2001.

(51) Int. Cl.$^7$ .................. C07D 251/16; C07D 251/18; A61K 31/53; A61P 35/00
(52) U.S. Cl. .................. 514/241; 544/211; 544/212; 544/213; 544/217; 544/219
(58) Field of Search ............................... 544/211, 212, 544/213, 217, 219; 514/241

(56) References Cited

U.S. PATENT DOCUMENTS

| 2,474,194 A | 6/1949 | Thurston |
| 3,136,816 A | 6/1964 | Cutler et al. |
| 3,226,394 A | 12/1965 | Schipper |
| 5,215,569 A | 6/1993 | Drewes et al. |
| 5,532,358 A | 7/1996 | Kelly |

FOREIGN PATENT DOCUMENTS

| CH | 261812 | 9/1949 |
| EP | 0 947 500 A1 | 10/1999 |
| FR | 2.168.227 | 8/1973 |
| GB | 1 390 235 | 4/1975 |
| JP | P2000-256358 A | 9/2000 |
| WO | WO 96/41795 | 12/1996 |
| WO | WO 97/19065 | 5/1997 |
| WO | WO 99/01136 | 1/1999 |
| WO | WO 99/31088 | 6/1999 |
| WO | WO 99/32477 | 7/1999 |
| WO | WO 99/62885 | 12/1999 |
| WO | WO 99/65909 | 12/1999 |
| WO | WO 00/27819 | 5/2000 |
| WO | WO 00/27820 | 5/2000 |
| WO | WO 00/39111 | 7/2000 |
| WO | WO 00/39117 | 7/2000 |
| WO | WO 00/43373 | 7/2000 |
| WO | WO 01/25220 | 4/2001 |

OTHER PUBLICATIONS

Hasan et al., Expert Opin. Biol. Ther. 1(4) 703–718, 2001.*
Pegram et al. Semin. Oncol. 29(3 Suppl. 11): 29–37.*
Cecil Textbook of Medicine, edited by Bennet, J.C., and Plum F., 20th edition, vol. 1, 1004–1010, 1996.*
Shapiro et al., (1957) "Guanamine Diuretics" J. Amer. Chem. Soc. 79: 5064–5071.
Konshin et al., (1981) "Synthesis and antimicrobial activity of arylamides of N–(4–pyridyl)anthranilc acid." Chem Abstr. 97:109837.
Singh et al., (1992) "Substituted Imidazolines and their CNS Activity" Ind. J. Het. Chem. 2:129–132.
Seto et al., (1993) "Molecular Self–Assembly through Hydrogen Bonding: Supramolecular Aggregates Based on the Cyanuric Acid•Melamine Lattice." J. Amer. Chem. Soc. 115:905–916.

* cited by examiner

Primary Examiner—Venkataraman Balasubramanian
(74) Attorney, Agent, or Firm—Joseph W. Bulock

(57) ABSTRACT

The invention encompasses compounds, analogs, prodrugs and pharmaceutically acceptable salts thereof, pharmaceutical compositions, uses and methods for prophylaxis and treatment of cancer and angiogenesis-related disease.

14 Claims, No Drawings

SUBSTITUTED TRIAZINYL AMIDE DERIVATIVES AND METHODS OF USE

This application claims the benefit of U.S. Provisional Application No. 60/282,977, filed Apr. 11, 2001, which is hereby incorporated by reference.

FIELD OF THE INVENTION

This invention is in the field of pharmaceutical agents and specifically relates to compounds, compositions, uses and methods for treating cancer and angiogenesis-related disorders.

BACKGROUND OF THE INVENTION

Phosphoryl transferases are a large family of enzymes that transfer phosphorous-containing groups from one substrate to another. Kinases are a class of enzymes that function in the catalysis of phosphoryl transfer. The protein kinases constitute the largest subfamily of structurally related phosphoryl transferases and are responsible for the control of a wide variety of signal transduction processes within the cell. Almost all kinases contain a similar 250–300 amino acid catalytic domain. The protein kinases may be categorized into families by the substrates they phosphorylate (e.g., protein-tyrosine, protein-serine/threonine, etc.). Protein kinase sequence motifs have been identified that generally correspond to each of these kinase families. Lipid kinases (e.g. PI3K) constitute a separate group of kinases with structural similarity to protein kinases.

The "kinase domain" appears in a number of polypeptides which serve a variety of functions. Such polypeptides include, for example, transmembrane receptors, intracellular receptor associated polypeptides, cytoplasmic located polypeptides, nuclear located polypeptides and subcellular located polypeptides. The activity of protein kinases can be regulated by a variety of mechanisms. It must be noted, however, that an individual protein kinase may be regulated by more than one mechanism. These mechanisms include, for example, autophosphorylation, transphosphorylation by other kinases, protein-protein interactions, protein-lipid interactions, protein-polynucleotide interactions, ligand binding, and post-translational modification.

Protein and lipid kinases regulate many different cell processes including, but not limited to, proliferation, growth, differentiation, metabolism, cell cycle events, apoptosis, motility, transcription, translation and other signaling processes, by adding phosphate groups to targets such as proteins or lipids. Phosphorylation events catalyzed by kinases act as molecular on/off switches that can modulate or regulate the biological function of the target protein. Phosphorylation of target proteins occurs in response to a variety of extracellular signals (hormones, neurotransmitters, growth and differentiation factors, etc.), cell cycle events, environmental or nutritional stresses, etc. Protein and lipid kinases can function in signaling pathways to activate or inactivate, or modulate the activity of (either directly or indirectly) the targets. These targets may include, for example, metabolic enzymes, regulatory proteins, receptors, cytoskeletal proteins, ion channels or pumps, or transcription factors. Uncontrolled signaling due to defective control of protein phosphorylation has been implicated in a number of diseases and disease conditions, including, for example, inflammation, cancer, allergy/asthma, disease and conditions of the immune system, disease and conditions of the central nervous system (CNS), cardiovascular disease, dermatology, and angiogenesis.

Initial interest in protein kinases as pharmacological targets was stimulated by the findings that many viral oncogenes encode structurally modified cellular protein kinases with constitutive enzyme activity. These findings pointed to the potential involvement of oncogene related protein kinases in human proliferative disorders. Subsequently, deregulated protein kinase activity, resulting from a variety of more subtle mechanisms, has been implicated in the pathophysiology of a number of important human disorders including, for example, cancer, CNS conditions, and immunologically related diseases. The development of selective protein kinase inhibitors that can block the disease pathologies and/or symptoms resulting from aberrant protein kinase activity has therefore generated much interest.

Protein kinases represent a large family of proteins which play a central role in the regulation of a wide variety of cellular processes, maintaining control over cellular function. A partial list of such kinases includes ab1, Atk, bcr-ab1, Blk, Brk, Btk, c-kit, c-met, c-src, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor" (=VEGF; originally termed 'Vascular Permeability Factor", =VPF), along with its cellular receptors.

VEGF is a dimeric, disulfide-linked 46-kDa glycoprotein related to "Platelet-Derived Growth Factor" (PDGF). It is produced by normal cell lines and tumor cell lines, is an endothelial cell-specific mitogen, shows angiogenic activity in in vivo test systems (e.g. rabbit cornea), is chemotactic for endothelial cells and monocytes, and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PLGF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors.

This has led to the hypothesis that the VEGF released by tumor cells could stimulate the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors which grow beyond a diameter of about 1–2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between apoptosis and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels.

U.S. Pat. No. 5,215,569, issued Jun. 1, 1993, describes substituted pyridines as herbicides. WO99/01136 describes substituted imidazoles as p38 inhibitors. WO00/43373 describes pyrimidinones as kinase inhibitors. Shapiro et al. (J. Amer. Chem.Soc., 79, 5064–71 (1957)) describe guanamines as potential diuretics. U.S. Pat. No. 3,136,816, issued Jun. 9, 1964, describe guanamines as potential diuretics. WO99/65909 describes pyrrolopyrimidine compounds as kinase inhibitors. WO97/19065 describes anilinopyrimidines as kinase inhibitors. U.S. Pat. No. 2,474,194, issued Jun. 21, 1949, describe guanamines as plastic additives. Swiss patent 261812 describes the preparation of triazines. British patent 1,390,235 describes trisubstituted triazines as agents for the treatment of the hormone system.

Schipper U.S. Pat. No. 3,226,394, issued Dec. 28, 1965, describes anthranilamides as CNS depressants. Japanese patent JP2000256358 describes pyrazole derivatives that block the calcium release-activated calcium channel. EP application 9475000, published Oct. 6, 1999, describes compounds as $PGE_2$ antagonists. PCT publication WO96/41795, published 27 Dec. 1996, describes benzamides as vasopressin antagonists.

U.S. Pat. No. 5,532,358, issued Jul. 2, 1996, describes the preparation of 2-(cyclopropylamino)-N-(2-methoxy-4-methyl-3-pyridinyl)-3-pyridinecarboxamide as an intermediate for HIV inhibitors. Triazine-substituted amines are described for their aggregating ability (J. Amer. Chem. Soc., 115, 905–16 (1993). Substituted imidazolines were tested for their antidepressant activity in Ind. J. Het. Chem., 2, 129–32 (1992). N-(4-Pyridyl)anthranilic amides were described in Chem Abstr. 97:109837 (1981). PCT publication WO99/32477, published 1 Jul. 1999, describes anthranilamides as anti-coagulants. PCT publication WO99/62885, published 9 Dec. 1999, describes 1-(4-aminophenyl) pyrazoles as antiinflammatories. PCT publication WO00/39111, published 6 Jul. 2000, describes amides as factor Xa inhibitors. PCT publication WO00/39117, published 6 Jul. 2000, describes heteroaromatic amides as factor Xa inhibitors. PCT publication WO00/27819, published 18 May 2000, describes anthranilic acid amides as VEGF inhibitors. PCT publication WO00/27820 published 18 May 2000, describes N-aryl anthranilic acid amides as VEGF inhibitors. 7-Chloroquinolinylamines are described in FR2168227 as antiinflammatories.

However, compounds of the current invention have not been described as inhibitors of angiogenesis such as for the treatment of cancer.

DESCRIPTION OF THE INVENTION

A class of compounds useful in treating cancer and angiogenesis is defined by Formula I

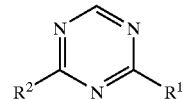

I wherein $R^1$ is selected from
    phenyl substituted with $R^{4a}$ and optionally substituted with 1–4 $R^4$, and
    heteroaryl substituted with $R^{4a}$ and optionally substituted with 1–4 $R^4$ on each ring;
    preferably phenyl substituted with $R^{4a}$ and optionally substituted with 1–3 $R^4$, and
        5–10 membered heteroaryl substituted with $R^{4a}$ and optionally substituted with 1–3 $R^4$;
        more preferably phenyl ortho-substituted with $R^{4a}$ and optionally substituted with $R^4$; and
        5–10 membered heteroaryl ortho substituted with $R^{4a}$ and optionally substituted with $R^4$;
        even more preferably phenyl ortho substituted with $R^{4a}$, and
            heteroaryl selected from isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, and benzthiazolyl, wherein heteroaryl is ortho-substituted with $R^{4a}$;
wherein $R^2$ is independently selected from H,
  halo,
  $R^3$,
  $R^8$,
  —$NHR^3$,
  —$NHR^5$,
  —$NHR^6$,
  —$NR^5R^5$,
  —$NR^5R^6$,
  —$SR^5$,
  —$SR^6$,
  —$SR^3$,
  —$OR^5$,
  —$OR^6$,
  —$OR^3$,
  —$C(O)R^3$,
  heterocyclyl optionally substituted with 1–4 independent $R^4$ on each ring, and $C_1$–$C_{10}$ alkyl optionally substituted with 1–4 independent $R^4$;

preferably halo,
$R^3$,
$R^8$,
—$NHR^3$,
—$NHR^5$,
—$NHR^6$,
—$NR^5R^5$,
—$NR^5R^6$,
—$SR^5$,
—$SR^6$,
—$SR^3$,
—$OR^5$,
—$OR^6$,
—$OR^3$,
—$C(O)R^3$,
4–10 membered heterocyclyl optionally substituted with 1–4 independent $R^4$, and
$C_1$–$C_4$ alkyl optionally substituted with 1–3 independent $R^4$;

more preferably halo,
—$NHR^3$,
—$NHR^5$,
—$NHR^6$,
—$NR^5R^5$,
6–10 membered heterocyclyl optionally substituted with 1–2 independent $R^4$, and
$C_1$–$C_2$ alkyl optionally substituted with 1–3 substituents independently selected from phenyl, $R^8$, chloro, fluoro, $OR^5$, $OC(O)R^5$, $NR^5R^5$ and $COOR^5$;
even more preferably fluoro, chloro, bromo, —$NHR^5$, and methyl optionally substituted with a radical selected from phenyl, $R^9$, chloro, fluoro, $OR^5$, $OC(O)R^5$, $NR^5R^5$ and $COOR^5$;

wherein $R^3$ is independently selected from
phenyl optionally substituted with 1–5 independent $R^4$, and
heteroaryl optionally substituted with 1–4 independent $R^4$;

preferably phenyl optionally substituted with 1–3 independent $R^4$, and
heteroaryl optionally substituted with 1–2 independent $R^4$; and
more preferably phenyl optionally substituted with $R^4$, and
5–10 membered heteroaryl optionally substituted with $R^4$;

wherein $R^4$ is independently selected from H,
$C_1$–$C_{10}$ alkyl,
$C_2$–$C_{10}$ alkenyl,
$C_2$–$C_{10}$ alkynyl,
$C_3$–$C_{10}$ cycloalkyl,
$C_4$–$C_{10}$ cycloalkenyl,
aryl,
$R^8$,
halo,
$SR^5$,
$OR^5$,
$OC(O)R^5$,
$NR^5R^5$,
$NR^5R^6$,
$NR^5R^{16}$,
$COOR^5$,
$NO_2$,
CN,
$C(O)R^5$,
$C(O)C(O)R^5$,
$C(O)NR^5R^5$,
$S(O)_nR^5$,
$S(O)_nNR^5R^5$,
$NR^5C(O)NR^5R^5$,
$NR^5C(O)C(O)R^5$,
$NR^5C(O)R^5$,
$NR^5(COOR^5)$,
$NR^5C(O)R^8$,
$NR^5S(O)_nNR^5R^5$,
$NR^5S(O)_nR^5$,
$NR^5S(O)_nR^8$,
$NR^5C(O)C(O)NR^5R^5$,
$NR^5C(O)C(O)NR^5R^6$,
$OC(O)NR^5R^5$,
$OS(O)_nNR^5R^5$,
$NR^5S(O)_nOR^5$,
$P(O)(OR^5)_2$,
$C_1$–$C_{10}$ alkyl substituted with 1–3 substituents independently selected from aryl, $R^7$ and $R^8$, and
$C_2$–$C_{10}$ alkenyl substituted with 1–3 substituents substituents independently selected from aryl, $R^7$ and $R^8$;

preferably H,
$C_1$–$C_6$ alkyl,
$C_2$–$C_6$ alkenyl,
$C_2$–$C_6$ alkynyl,
$C_3$–$C_6$ cycloalkyl,
$C_4$–$C_6$ cycloalkenyl,
phenyl,
$R^8$,
halo selected from fluoro and chloro,
$SR^5$,
$OR^5$,
$OC(O)R^5$,
$NR^5R^5$,
$NR^5R^6$,
$NR^5R^{16}$,
$COOR^5$,
$NO_2$,
CN,
$C(O)C(O)R^5$,
$C(O)NR^5R^5$,
$S(O)_nR^5$,
$S(O)_nNR^5R^5$,
$NR^5C(O)NR^5R^5$,
$NR^5C(O)C(O)R^5$,
$NR^5C(O)R^5$,
$NR^5(COOR^5)$,
$NR^5C(O)R^8$,
$NR^5S(O)_nNR^5R^5$,
$NR^5S(O)_nR^5$,
$NR^5S(O)_nR^8$,
$NR^5C(O)C(O)NR^5R^5$,
$NR^5C(O)C(O)NR^5R^6$,
$OC(O)NR^5R^5$, $OS(O)_nNR^5R^5$,
$NR^5S(O)_nOR^5$,
$C_1-C_6$ alkyl substituted with 1–3 substituents independently selected from phenyl, $R^7$ and $R^8$; and
$C_2-C_6$ alkenyl substituted with 1–3 substituents independently selected from phenyl, $R^7$ or $R^8$;
more preferably H,
  $C_1-C_4$ alkyl,
  $C_2-C_4$ alkenyl,
  $C_2-C_4$ alkynyl,
  $C_3-C_6$ cycloalkyl,
  phenyl,
  $R^8$,
  chloro,
  fluoro,
  $OR^5$,
  $OC(O)R^5$,
  $NR^5R^5$,
  $NR^5R^6$,
  $NR^5R^{16}$,
  $COOR^5$,
  $NO_2$,
  CN,
  $C(O)R^5$,
  $C(O)NR^5R^5$,
  $S(O)_nR^5$,
  $S(O)_nNR^5R^5$,
  $NR^5C(O)R^5$,
  $NR^5(COOR^5)$,
  $NR^5C(O)R^8$,
  $NR^5S(O)_nR^5$,
  $NR^5S(O)_nR^8$,
  $NR^5S(O)_nOR^5$,
  $C_1-C_4$ alkyl substituted with 1–3 substituents independently selected from phenyl, $R^7$ and $R^8$; and
  $C_2-C_4$ alkenyl substituted with 1–3 substituents independently selected from phenyl, $R^7$ and $R^8$;
  even more preferably $C_1-C_4$ alkyl, optionally substituted phenyl, chloro, fluoro, $OR^5$, and $C_1-C_4$ alkyl substituted with 1–3 substituents independently selected from optionally substituted phenyl and $R^8$;
wherein $R^{4a}$ is $-NR^5R^{16}$ or $-CH_2NR^5R^{16}$;
  preferably $-NR^5R^{16}$; and
  more preferably $-NHR^{16}$;
wherein $R^5$ is independently selected from
H,
$C_1-C_{10}$ alkyl,
$C_2-C_{10}$ alkenyl,
$C_2-C_{10}$ alkynyl,
$C_3-C_{10}$ cycloalkyl,
$C_4-C_{10}$ cycloalkenyl,
aryl,
$R^9$,
$C_1-C_{10}$ alkyl substituted with 1–3 substituents independently selected from aryl, $R^7$ or $R^9$ groups;
$C_3-C_{10}$ cycloalkyl substituted with 1–3 substituents independently selected from aryl, $R^7$ or $R^9$ groups; and
$C_2-C_{10}$ alkenyl substituted with 1–3 substituents independently selected from aryl, $R^7$ or $R^9$;
preferably H,
  $C_1-C_6$ alkyl,
  $C_2-C_6$ alkenyl,
  $C_2-C_6$ alkynyl,
  $C_3-C_6$ cycloalkyl,
  $C_4-C_6$ cycloalkenyl,
  phenyl,
  $R^9$,
  $C_1-C_6$ alkyl substituted with 1–3 substituents independently selected from phenyl, $R^7$ or $R^9$ groups,
  $C_3-C_6$ cycloalkyl substituted with 1–3 substituents independently selected from phenyl, $R^7$ and $R^9$ groups, and
  $C_2-C_6$ alkenyl substituted with 1–3 substituents independently selected from phenyl, $R^7$ and $R^9$;
more preferably H,
  $C_1-C_4$ alkyl,
  $C_3-C_6$ cycloalkyl,
  phenyl,
  $R^9$,
  $C_1-C_4$ alkyl substituted with 1–3 substituents independently selected from aryl, $R^7$ or $R^9$ groups, and
  $C_3-C_{10}$ cycloalkyl substituted with 1–3 substituents independently selected from aryl, $R^7$ or $R^9$ groups; and
even more preferably H,
  $C_1-C_4$ alkyl,
  $C_3-C_4$ cycloalkyl,
  optionally substituted phenyl,
  $R^9$, and
  $C_1-C_3$ alkyl substituted with 1–3 substituents independently selected from optionally substituted phenyl, $R^7$ or $R^9$ groups;
wherein $R^{5a}$ is aryl and $R^9$;
  preferably optionally substituted phenyl and $R^{9a}$;
wherein $R^6$ is independently selected from $C(O)R^5$, $COOR^5$, $C(O)NR^5R^5$, $C(=NR^5)NR^5R^5$, and $S(O)_nR^5$;
  preferably $C(O)R^5$;
wherein $R^7$ is independently selected from halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_nNR^{10}R^{10}$, $NR^{10}S(O)_nNR^{10}R^{10}$, $NR^{10}S(O)_nR^{10}$, and $P(O)(OR^5)_2$;
  preferably chloro, fluoro, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10}))(COOR^{10})$, $S(O)_nNR^{10}R^{10}$, $NR^{10}S(O)_nNR^{10}R^{10}$ and $NR^{10}S(O)_nR^{10}$;
  more preferably chloro, fluoro, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, $C(O)NR^{10}R^{10}$, $N(R^{10})C(O)R^{10}$, $S(O)_nNR^{10}R^{10}$, and $NR^{10}S(O)_nR^{10}$;
  even more preferably chloro, fluoro, $CF_3$, $OR^{10}$, $NR^{10}R^{10}$, $COOR^{10}$, $NO_2$, CN, and $C(O)R^{10}$;
wherein $R^8$ is independently selected from 3–8 membered monocyclic, 7–12 membered bicyclic, and 11–14 membered tricyclic ring system comprising 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2, 3 or 4 atoms of each ring may be substituted by a substituent independently selected from $C_1-C_{10}$ alkyl, $C_2-C_{10}$ alkenyl, $C_2-C_{10}$ alkynyl, $C_3-C_{10}$ cycloalkyl, $C_4-C_{10}$ cycloalkenyl, aryl, $R^9$, halo, sulfo, oxo, $SR^5$, $OR^5$, $OC(O)R^5$, $NR^5R^5$, $NR^5R^6$, $NR^6R^6$, $COOR^5$, $NO_2$, CN, $C(O)R^5$, $C(O)NR^5R^5$, $S(O)_nNR^5R^5$, $NR^5C(O)NR^5R^5$, $NR^5C(O)R^9$, $NR^5S(O)_nNR^5R^5$, $NR^5S(O)_nR^9$, $C_1-C_{10}$ alkyl substituted with 1–3 substituents independently selected from $R^7$, $R^9$ and aryl; and $C_2-C_{10}$ alkenyl substituted with 1–3 substituents independently selected from $R^7$, $R^9$ and aryl;
  preferably 3–8 membered monocyclic, and 7–12 membered bicyclic ring system comprising 1–3 heteroatoms if monocyclic, or 1–6 heteroatoms if bicyclic, said heteroatoms independently selected from O, N, or S, which may be saturated or unsaturated, and wherein 0, 1, 2, 3 or 4 atoms of each ring may be substituted by substituents independently selected from $C_1$–$C_6$ alkyl, $C_2$–$C_6$ alkenyl, $C_2$–$C_6$ alkynyl, $C_3$–$C_6$ cycloalkyl, $C_4$–$C_6$ cycloalkenyl, phenyl, $R^9$, chloro, fluoro, oxo, $SR^5$, $OR^5$, $OC(O)R^5$, $NR^5R^5$, $NR^5R^6$, $NR^6R^6$, $COOR^5$, $NO_2$, $CN$, $C(O)R^5$, $C(O)NR^5R^5$, $S(O)_nNR^5R^5$, $NR^5C(O)NR^5R^5$, $NR^5C(O)R^9$, $NR^5S(O)_nNR^5R^5$, $NR^5S(O)_nR^9$, $C_1$–$C_6$ alkyl
substituted with 1–3 substituents independently selected from $R^7$, $R^9$ and phenyl, and
$C_2$–$C_6$ alkenyl substituted with 1–3 substituents independently selected from $R^7$, $R^9$ and phenyl;
more preferably 3–8 membered monocyclic, and 7–12 membered bicyclic ring system comprising 1–3 heteroatoms if monocyclic, 1–6 heteroatoms if bicyclic, said heteroatoms independently selected from O, N, or S, which may be saturated or unsaturated, and wherein 0, 1, 2, 3 or 4 atoms of each ring may be substituted by a substituent independently selected from $C_1$–$C_4$ alkyl, $C_3$–$C_6$ cycloalkyl, $R^9$, phenyl, chloro, fluoro, oxo, $OR^5$, $OC(O)R^5$, $NR^5R^5$, $NR^5R^6$, $NR^6R^6$, $COOR^5$, $NO_2$, $CN$, $C(O)R^5$, $C(O)NR^5R^5$, $S(O)_nNR^5R^5$, $NR^5C(O)R^9$, $NR^5S(O)_nR^9$, and $C_1$–$C_4$ alkyl substituted with 1–3 substituents independently selected from $R^7$, $R^9$ and phenyl;
even more preferably 5–6 membered heteroaryl optionally substituted with $C_1$–$C_4$ alkyl, halo, $C_1$–$C_4$ haloalkyl, optionally substituted phenyl, $R^9$, $OR^5$, $NR^5R^5$, $COOR^5$, $C(O)R^5$, $OC(O)R^5$, and $C(O)NR^5R^5$;
wherein $R^{8a}$ is independently selected from 3–8 membered monocyclic, 7–12 membered bicyclic, and 11–14 membered tricyclic ring system comprising 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2, 3 or 4 atoms of each ring may be substituted by a substituent independently selected from $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, aryl, $R^9$, halo, sulfo, oxo, $SR$, $OR^5$, $OC(O)R^5$, $NR^5R^5$, $NR^5R^6$, $NR^6R^6$, $COOR^5$, $NO_2$, $CN$, $C(O)R^5$, $C(O)NR^5R^5$, $S(O)_nNR^5R^5$, $NR^5C(O)NR^5R^5$, $NR^5C(O)R^9$, $NR^5S(O)_nNR^5R^5$, $NR^5S(O)_nR^9$, $C_1$–$C_{10}$ alkyl substituted with 1–3 substituents independently selected from $R^7$, $R^9$ and aryl; and $C_2$–$C_{10}$ alkenyl substituted with 1–3 substituents independently selected from $R^7$, $R^9$ and aryl;
preferably selected from 5–6 membered monocyclic, or 9–10 membered bicyclic ring system, comprising 1–3 heteroatoms if monocyclic, or 1–6 heteroatoms if bicyclic, said heteroatoms independently selected from O, N, or S, which may be saturated or unsaturated, and wherein 0, 1, 2, 3 or 4 atoms of each ring may be substituted by substituents independently selected from $C_1$–$C_6$ alkyl, $C_2$–$C_6$ alkenyl, $C_2$–$C_6$ alkynyl, $C_3$–$C_6$ cycloalkyl, $C_4$–$C_6$ cycloalkenyl, phenyl, $R^9$, halo, oxo, $SR^5$, $OR^5$, $OC(O)R^5$, $NR^5R^5$, $NR^5R^6$, $NR^6R^6$, $COOR^5$, $NO_2$, $CN$, $C(O)R^5$, $C(O)NR^5R^5$, $S(O)_nNR^5R^5$, $NR^5C(O)R^9$, $NR^5S(O)_nR^9$, $C_1$–$C_6$ alkyl
substituted with 1–3 substituents independently selected from $R^7$, $R^9$ and phenyl, and
$C_2$–$C_6$ alkenyl substituted with 1–3 substituents independently selected from $R^7$, $R^9$ and phenyl;
provided $R^{8a}$ is substituted with $C(O)NHR^{5a}$;

preferably 5–6 membered monocyclic, or 9–10 membered bicyclic ring system, comprising 1–3 heteroatoms if monocyclic, or 1–6 heteroatoms if bicyclic, said heteroatoms independently selected from O, N, or S, which may be partially saturated or unsaturated, and wherein 0, 1, 2, 3 or 4 atoms of each ring may be substituted by a substituent independently selected from $C_1$–$C_4$ alkyl, $C_3$–$C_6$ cycloalkyl, $R^9$, oxo, phenyl, chloro, fluoro, $OR^5$, $OC(O)R^5$, $NR^5R^5$, $NR^5R^6$, $COOR^5$, $NO_2$, $CN$, $C(O)R^5$, $C(O)NR^5R^5$, $S(O)_n NR^5R^5$, $NR^5C(O)R^9$, $NR^5S(O)_nR^9$, and $C_1$–$C_4$ alkyl substituted with 1–3 substituents independently selected from $R^7$, $R^9$ and phenyl;
provided $R^{8a}$ is substituted with $C(O)NHR^{5a}$;
more preferably 5–6 membered monocyclic heteroaryl, or 9–10 membered bicyclic heteroaryl comprising 1–2 heteroatoms if monocyclic, or 1–4 heteroatoms if bicyclic, said heteroatoms independently selected from O, N, or S, and wherein 0, 1, or 2 atoms of each ring may be substituted by substituents independently selected from $C_1$–$C_4$ alkyl, optionally substituted phenyl, $R^9$, chloro, fluoro, oxo, $OR^5$, and $C_1$–$C_4$ alkyl substituted with 1–3 substituents independently selected from $R^7$, $R^9$ and optionally substituted phenyl;
provided $R^{8a}$ is substituted with $C(O)NHR^{5a}$;
wherein $R^9$ is independently a 3–8 membered monocyclic, 7–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2 or 3 atoms of each ring may be substituted by a substituent independently selected from $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, halo, sulfo, oxo, haloalkyl, $SR^{10}$, $OR^{10}$, $NR^{10}R^{10}$, $NR^{10}R^{11}$, $NR^{11}R^{11}$, $COOR^{10}$, $NO_2$, $CN$, $C(O)R^{10}$, $S(O)_nR^{10}$, $S(O)_nNR^{10}R^{10}$, and $C(O)NR^{10}R^{10}$;
preferably 3–8 membered monocyclic, a 7–12 membered bicyclic, ring system comprising 1–3 heteroatoms if monocyclic, or 1–6 heteroatoms if bicyclic, said heteroatoms independently selected from O, N, or S, which may be saturated or unsaturated, and wherein 0, 1, 2 or 3 atoms of each ring may be substituted by a substituent independently selected from $C_1$–$C_6$ alkyl, $C_3$–$C_6$ cycloalkyl, halo, oxo, $C_{1-6}$ haloalkyl, $OR^{10}$, $NR^{10}R^{10}$, $NR^{10}R^{11}$, $COOR^{10}$, $NO_2$, $CN$, $C(O)R^{10}$, $S(O)_nR^{10}$, $S(O)_nNR^{10}R^{10}$, and $C(O)NR^{10}R^{10}$;
more preferably 3–8 membered monocyclic, or 7–12 membered bicyclic, ring system comprising 1–3 heteroatoms if monocyclic or 1–6 heteroatoms if bicyclic, said heteroatoms independently selected from O, N, or S, which may be saturated or unsaturated, and wherein 0, 1, 2 or 3 atoms of each ring may be substituted by a substituent independently selected from $C_1$–$C_4$ alkyl, $C_3$–$C_6$ cycloalkyl, fluoro, chloro, oxo, $C_1$–$C_4$ haloalkyl, $OR^{10}$, $NR^{10}R^{10}$, $NR^{10}R^{11}$, $COOR^{10}$, $NO_2$, $CN$, $C(O)R^{10}$, $S(O)_nR^{10}$, $S(O)_nNR^{10}R^{10}$, and $C(O)NR^{10}R^{10}$;
even more preferably 5–6 membered heteroaryl, or 9–10 membered bicyclic heteroaryl comprising 1–2 heteroatoms if monocyclic, 1–4 heteroatoms if bicyclic, said heteroatoms independently selected from O, N, or S, and wherein 0, 1, or 2 atoms of each ring may be substituted by a substituent independently selected from $C_1$–$C_4$ alkyl, halo, $C_1$–$C_4$ haloalkyl, optionally substituted phenyl, $R^8$, $OR^{10}$, $NR^{10}R^{10}$, $COOR^{10}$, $C(O)R^{10}$, $OC(O)R^{10}$, and $C(O)NR^{10}R^{10}$;

wherein $R^{9a}$ is independently a 5–6 membered monocyclic, or 9–10 membered bicyclic ring system comprising 1–3 heteroatoms if monocyclic, or 1–6 heteroatoms if bicyclic, said heteroatoms independently selected from O, N, or S, which may be saturated or unsaturated, and wherein 0, 1, 2 or 3 atoms of each ring may be substituted by a substituent independently selected from $C_1$–$C_6$ alkyl, $C_2$–$C_6$ alkenyl, $C_2$–$C_6$ alkynyl, $C_3$–$C_6$ cycloalkyl, $C_4$–$C_6$ cycloalkenyl, halo, oxo, $C_{1-6}$ haloalkyl, $SR^{10}$, $OR^{10}$, $NR^{10}R^{10}$, $NR^{10}R^{11}$, $NR^{11}R^{11}$, $COOR^{10}$, $NO_2$, CN, $C(O)R_{10}$, $S(O)_nR^{10}$, $S(O)_nNR^{10}R^{10}$, and $C(O)NR^{10}R^{10}$;

preferably 3–8 membered monocyclic, or 7–12 membered bicyclic ring system comprising 1–3 heteroatoms if monocyclic, or 1–6 heteroatoms if bicyclic, said heteroatoms independently selected from O, N, or S, which may be saturated or unsaturated, and wherein 0, 1, 2 or 3 atoms of each ring may be substituted by a substituent independently selected from $C_1$–$C_4$ alkyl, $C_2$–$C_4$ alkenyl, $C_2$–$C_4$ alkynyl, $C_3$–$C_6$ cycloalkyl, $C_4$–$C_6$ cycloalkenyl, oxo, chloro, fluoro, $C_1$–$C_4$ haloalkyl, $SR^{10}$, $OR^{10}$, $NR^{10}R^{10}$, $NR^{10}R^{11}$, $NR^{11}R^{11}$, $COOR^{10}$, $NO_2$, CN, $C(O)R^{10}$, $S(O)_nR^{10}$, $S(O)_nNR^{10}R^{10}$, and $C(O)NR^{10}R^{10}$;

more preferably 5–6 membered monocyclic, or 9–10 membered bicyclic ring system comprising 1–2 heteroatoms if monocyclic, or 1–3 heteroatoms if bicyclic, said heteroatoms independently selected from O, N, or S, which may be saturated or unsaturated, and wherein 0, 1, or 2 atoms of each ring may be substituted by a substituent independently selected from $C_1$–$C_3$ alkyl, halo, oxo, $C_1$–$C_3$ haloalkyl and $OR^{10}$;

wherein $R^{10}$ is independently H; $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, haloalkyl, $C_1$–$C_{10}$ alkyl optionally substituted with 1–3 substituents independently selected from $C_2$–$C_{10}$ alkenyl, $C_2$–$C_{10}$ alkynyl, $C_3$–$C_{10}$ cycloalkyl, $C_4$–$C_{10}$ cycloalkenyl, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_nNR^{12}R^{12}$, and $OC(O)R^{12}$;
and phenyl optionally substituted with 1–3 substituents independently selected from $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_nNR^{12}R^{12}$, and $OC(O)R^{12}$;

preferably H, $C_1$–$C_6$ alkyl, $C_2$–$C_6$ alkenyl, $C_2$–$C_6$ alkynyl, $C_3$–$C_6$ cycloalkyl, $C_4$–$C_6$ cycloalkenyl, $C_1$–$C_6$ alkyl substituted with 1–3 independent, $C_2$–$C_{10}$ alkenyl, $C_2$–$C_{10}$ alkynyl, $C_3$–$C_{10}$ cycloalkyl, $C_4$–$C_{10}$ cycloalkenyl, halo, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_nNR^{12}R^{12}$ and $OC(O)R^{12}$, and phenyl optionally substituted with 1–3 substituents independently selected from $C_1$–$C_6$ alkyl, $C_2$–$C_6$ alkenyl, $C_2$–$C_6$ alkynyl, $C_3$–$C_6$ cycloalkyl, $C_4$–$C_6$ cycloalkenyl, halo, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_nNR^{12}R^{12}$, and $OC(O)R^{12}$;

more preferably H, $C_1$–$C_4$ alkyl, $C_3$–$C_6$ cycloalkyl, $C_1$–$C_4$ alkyl optionally substituted with 1–3 substituents independently selected from $C_2$–$C_4$ alkenyl, $C_2$–$C_4$ alkynyl, $C_3$–$C_6$ cycloalkyl, $OR^{12}$, $SR^{12}$, $NR^{12}R^2$, $COOR^{12}$, chloro, fluoro, $NO_2$, CN, $C(O)R^{12}$, $C(O)NR^{12}R^{12}$, $NR^{12}C(O)R^{12}$, $S(O)_nNR^{12}R^{12}$, and $OC(O)R^{12}$; and phenyl optionally substituted with 1–3 substituents independently selected from $C_1$–$C_4$ alkyl, $C_2$–$C_4$ alkenyl, $C_2$–$C_4$ alkynyl, $C_3$–$C_6$ cycloalkyl, $C_4$–$C_6$ cycloalkenyl, $OR^{12}$, $SR^{12}$, $NR^{12}R^{12}$, $COOR^{12}$, $NO_2$, CN, $C(O)R^{12}$, $C(O)NR^{12}R^{12}$, chloro, fluoro, $NR^{12}C(O)R^{12}$, $N(R^{12})(COOR^{12})$, $S(O)_nNR^{12}R^{12}$, and $OC(O)R^{12}$;

even more preferably H, methyl and $C_1$–$C_3$ alkyl substituted with 1–3 substituents independently selected from fluoro, chloro, hydroxy, methoxy, optionally substituted phenyl and $R^9$, and optionally substituted phenyl;

wherein $R^{11}$ is independently selected from $C(O)R^{10}$, $COOR^{10}$, $C(O)NR^{10}R^{10}$ and $S(O)_nR^{10}$;

wherein $R^{12}$ is independently selected from H, $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, $C_1$–$C_{10}$ alkyl substituted with 1–3 substituents independently selected from $C_2$–$C_{10}$ alkenyl, $C_2$–$C_{10}$ alkynyl, $C_3$–$C_{10}$ cycloalkyl, $C_4$–$C_{10}$ cycloalkenyl, halo, $OR^{13}$, $SR^{13}$, $NR^{13}R^{13}$, $COOR^{13}$, $NO_2$, CN, $C(O)R^{13}$, $C(O)NR^{13}R^{13}$, $NR^{13}C(O)R^{13}$, and $OC(O)R^{13}$, and phenyl optionally substituted with 1–3 substituents independently selected from $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, halo, $OR^{13}$, $SR^{13}$, $NR^{13}R^{13}$, $COOR^{13}$, $NO_2$, CN, $C(O)R^{13}$, $C(O)NR^{13}R^{13}$, $NR^{13}C(O)R^{13}$, and $OC(O)R^{13}$;

preferably H, $C_1$–$C_6$ alkyl, $C_3$–$C_6$ cycloalkyl, $C_1$–$C_6$ alkyl substituted with 1–3 substituents independently selected from $C_2$–$C_4$ alkenyl, $C_2$–$C_4$ alkynyl, $C_3$–$C_{10}$ cycloalkyl, $C_4$–$C_{10}$ cycloalkenyl, halo, $OR^{13}$, $NR^{13}R^{13}$, $COOR^{13}$, $NO_2$, CN, $C(O)R^{13}$, $C(O)NR^{13}R^{13}$, $NR^{13}C(O)R^{13}$, and $OC(O)R^{13}$, and phenyl optionally substituted with 1–3 substituents independently selected from $C_1$–$C_6$ alkyl, $C_2$–$C_6$ alkenyl, $C_2$–$C_6$ alkynyl, halo, $OR^{13}$, $NR^{13}R^{13}$, $COOR^{13}$, $NO_2$, CN, $C(O)R^{13}$, $C(O)NR^{13}R^{13}$, $NR^{13}C(O)R^{13}$, and $OC(O)R^{13}$;

more preferably H, $C_1$–$C_4$ alkyl, $C_3$–$C_6$ cycloalkyl, $C_1$–$C_4$ alkyl substituted with 1–3 substituents independently selected from $C_2$–$C_4$ alkenyl, $C_2$–$C_4$ alkynyl, $C_3$–$C_6$ cycloalkyl, $OR^{13}$, $SR^{13}$, fluoro, chloro, $NR^{13}R^{13}$, $COOR^{13}$, $NO_2$, CN, $C(O)R^{13}$, $C(O)NR^{13}R^{13}$, $NR^{13}C(O)R^{13}$, and $OC(O)R^{13}$, and phenyl optionally substituted with 1–3 substituents independently selected from $C_1$–$C_4$ alkyl, $C_2$–$C_4$ alkenyl, $C_2$–$C_4$ alkynyl, $C_3$–$C_6$ cycloalkyl, $C_4$–$C_6$ cycloalkenyl, $CF_3$, $OR^{13}$, $SR^{13}$, $NR^{13}R^{13}$, $COOR^{13}$, fluoro, chloro, $NO_2$, CN, $C(O)R^{13}$, $C(O)NR^{13}R^{13}$, $NR^{13}C(O)R^{13}$, and $OC(O)R^{13}$;

wherein $R^{13}$ is independently selected from H, $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, $C_1$–$C_{10}$ alkyl optionally substituted with halo, $OR^{14}$, $SR^{14}$, $NR^{14}R^{14}$, $COOR^{14}$, $NO_2$, and CN, and phenyl optionally substituted with halo, $CF_3$, $OR^{14}$, $SR^{14}$, $NR^{14}R^{14}$, $COOR^{14}$, $NO_2$, and CN;

preferably H, $C_1$–$C_6$ alkyl, $C_3$–$C_6$ cycloalkyl, $C_1$–$C_6$ alkyl optionally substituted with halo, $CF_3$, $OR^{14}$, $NR^{14}R^{14}$, $COOR^{14}$, $NO_2$, and CN, and phenyl optionally substituted with halo, $OR^{14}$, $NR^{14}R^{14}$, $COOR^{14}$, $NO_2$, and CN;

more preferably H, $C_1$–$C_4$ alkyl, $C_3$–$C_6$ cycloalkyl, $C_1$–$C_4$ alkyl optionally substituted with $OR^{14}$, $NR^{14}R^{14}$, and $COOR^{14}$, and phenyl optionally substituted with halo, $CF_3$, $OR^{14}$, $NR^{14}R^{14}$, and $COOR^{14}$;

wherein R$^{14}$ is independently selected from H, C$_1$–C$_{10}$ alkyl, C$_3$–C$_{10}$ cycloalkyl and phenyl;
  preferably H, C$_1$–C$_6$ alkyl, C$_3$–C$_6$ cycloalkyl and phenyl; more preferably H, C$_1$–C$_4$ alkyl, C$_3$–C$_6$ cycloalkyl and phenyl;
wherein R$^{16}$ is independently selected from C$_4$–C$_{10}$ cycloalkenyl, aryl, and R$^8$; provided aryl is substituted with C(O)NHR$^{5a}$;
  preferably phenyl and R$^{8a}$; provided phenyl is substituted with C(O)NHR$^{5a}$;
wherein n is independently 1 or 2;
  preferably 2; and
wherein aryl is independently a 6-carbon monocyclic, 10-carbon bicyclic or 14-carbon tricyclic aromatic ring system optionally substituted with 1–3 substituents independently selected from C$_1$–C$_{10}$ alkyl, C$_2$–C$_{10}$ alkenyl, C$_2$–C$_{10}$ alkynyl, C$_3$–C$_{10}$ cycloalkyl, C$_4$–C$_{10}$ cycloalkenyl, R$^9$, halo, haloalkyl, CF$_3$, OR$^{10}$, SR$^{10}$, NR$^{10}$R$^{10}$, NR$^{10}$R$^{11}$, COOR$^{10}$, NO$_2$, CN, C(O)R$^{10}$, C(O)C(O)R$^{10}$, C(O)NR$^5$R$^5$, N(R$^{10}$)C(O)NR$^{10}$R$^{10}$, N(R$^{10}$)C(O)R$^{10}$R, N(R$^{10}$)S(O)$_n$R$^{10}$, N(R$^{10}$)(COOR$^{10}$), NR$^{10}$C(O)C(O)R$^{10}$, NR$^{10}$C(O)R$^{10}$, NR$^{10}$S(O)$_n$NR$^{10}$R$^{10}$, NR$^{10}$S(O)$_n$R$^9$, NR$^{12}$C(O)C(O)NR$^{12}$R$^{12}$, S(O)$_n$R$^{10}$, S(O)$_n$NR$^{10}$R$^{10}$, OC(O)R$^{10}$, C$_1$–C$_{10}$ alkyl substituted with 1–3 substituents independently selected from R$^9$, halo, CF$_3$, OR$^{10}$, SR$^{10}$, OC(O)R$^{10}$, NR$^{11}$R$^{11}$, NR$^{10}$R$^{10}$, NR$^{10}$R$^{11}$, COOR$^{10}$, NO$_2$, CN, C(O)R$^{10}$, OC(O)NR$^{10}$R$^{10}$, C(O)NR$^5$R$^5$, N(R$^{10}$)C(O)R$^{10}$, N(R$^{10}$)(COOR$^{10}$), S(O)$_n$NR$^{10}$R$^{10}$; R$^{10}$; and
  C$_2$–C$_{10}$ alkenyl substituted with 1–3 substituents independently selected from R$^9$, halo, CF$_3$, OR$^{10}$, SR$^{10}$, OC(O)R$^{10}$, NR$^{11}$R$^{11}$, NR$^{10}$R$^{10}$, NR$^{10}$R$^{11}$, COOR$^{10}$, NO$_2$, CN, C(O)R$^{10}$, OC(O)NR$^{10}$R$^{10}$, C(O)NR$^{10}$R$^{10}$, N(R$^{10}$)C(O)R$^{10}$, N(R$^{10}$)(COOR$^{10}$) and S(O)$_n$NR$^{10}$R$^{10}$;
  preferably phenyl is optionally substituted with 1–3 substituents independently selected from C$_1$–C$_6$ alkyl, C$_2$–C$_6$ alkenyl, C$_2$–C$_6$ alkynyl, C$_3$–C$_6$ cycloalkyl, C$_4$–C$_6$ cycloalkenyl, R$^9$, halo, CF$_3$, OR$^{10}$, SR$^{10}$, NR$^{10}$R$^{10}$, NR$^{10}$R$^{11}$, COOR$^{10}$, NO$_2$, CN, C(O)R$^{10}$, C(O)C(O)R$^{10}$, C(O)NR$^5$R$^5$, N(R$^{10}$)C(O)NR$^{10}$R$^{10}$, N(R$^{10}$)C(O)R$^{10}$, N(R$^{10}$)S(O)$_n$R$^{10}$, N(R$^{10}$)(COOR$^{10}$), NR$^{10}$C(O)C(O)R$^{10}$, NR$^{10}$C(O)R$^9$, NR$^{10}$S(O)$_n$NR$^{10}$R$^{10}$, NR$^{10}$S(O)$_n$R$^9$, NR$^{12}$C(O)C(O)NR$^{12}$R$^{12}$, S(O)$_n$R$^{10}$, S(O)$_n$NR$^{10}$R$^{10}$, OC(O)R$^{10}$, C$_1$–C$_6$ alkyl substituted with 1–3 substituents independently selected from R$^9$, halo, OR$^{10}$, SR$^{10}$, OC(O)R$^{10}$, NR$^{11}$R$^{11}$, NR$^{10}$R$^{10}$, NR$^{10}$R$^{11}$, COOR$^{10}$, NO$_2$, CN, C(O)R$^{10}$, OC(O)NR$^{10}$R$^{10}$, C(O)NR$^5$R$^5$, N(R$^{10}$)C(O)R$^{10}$, N(R$^{10}$)(COOR$^{10}$), and S(O)$_n$NR$^{10}$R$^{10}$; and
  C$_2$–C$_6$ alkenyl substituted with 1–3 substituents independently selected from R$^9$, halo, CF$_3$, OR$^{10}$, SR$^{10}$, OC(O)R$^{10}$, NR$^{11}$R$^{11}$, NR$^{10}$R$^{10}$, NR$^{10}$R$^{11}$, COOR$^{10}$, NO$_2$, CN, C(O)R$^{10}$, OC(O)NR$^{10}$R$^{10}$, C(O)NR$^{10}$R$^{10}$, N(R$^{10}$)C(O)R$^{10}$, N(R$^{10}$)(COOR$^{10}$) and S(O)$_n$NR$^{10}$R$^{10}$;
    more preferably optionally substituted phenyl is optionally substituted with 1–3 substituents independently selected from C$_1$–C$_4$ alkyl, C$_2$–C$_4$ alkenyl, C$_2$–C$_4$ alkynyl, C$_3$–C$_6$ cycloalkyl, R$^9$, C$_1$–C$_4$, haloalkyl, fluoro, chloro, OR$^{10}$, NR$^{10}$R$^{10}$, NR$^{10}$R$^{11}$, COOR$^{10}$, NO$_2$, CN, C(O)R$^{10}$, C(O)NR$^5$R$^5$, N(R$^{10}$)C(O)R$^{10}$, N(R$^{10}$)S(O)$_n$R$^{10}$, NR$^{10}$C(O)R$^9$, NR$^{10}$S(O)$_n$R$^9$, S(O)$_n$R$^{10}$, S(O)$_n$NR$^{10}$R$^{10}$, OC(O)R$^{10}$, C$_1$–C$_4$ alkyl substituted with 1–3 substituents independently selected from R$^9$, fluoro, chloro, OR$^{10}$, SR$^{10}$, OC(O)R$^{10}$, NR$^{11}$R$^{11}$, NR$^{10}$R$^{10}$, NR$^{10}$R$^{11}$, COOR$^{10}$, NO$_2$, CN, C(O)R$^{10}$, OC(O)NR$^{10}$R$^{10}$, C(O)NR$^5$R$^5$, N(R$^{10}$)C(O)R$^{10}$, and S(O)$_n$NR$^{10}$R$^{10}$; and
    C$_2$–C$_4$ alkenyl substituted with 1–3 substituents independently selected from R$^9$, halo, OR$^{10}$, SR$^{10}$, OC(O)R$^{10}$, NR$^{11}$R$^{11}$, NR$^{10}$R$^{10}$, NR$^{10}$R$^{11}$, COOR$^{10}$, NO$_2$, CN, C(O)R$^{10}$, OC(O)NR$^{10}$R$^{10}$, C(O)NR$^{10}$R$^{10}$, N(R$^{10}$)C(O)R$^{10}$, and S(O)$_n$NR$^{10}$R$^{10}$; and
    even more preferably phenyl is optionally substituted with 1–3 substituents independently selected from C$_1$–C$_3$ alkyl, R$^9$, fluoro, chloro, C$_1$–C$_3$ haloalkyl, OR$^{10}$, NR$^{10}$R$^{10}$, COOR$^{10}$, C(O)R$^{10}$, C(O)NR$^5$R$^5$, OC(O)R$^{10}$, and C$_1$–C$_3$ alkyl substituted with 1–2 substituents independently selected from phenyl and R$^9$;
and pharmaceutically acceptable salts thereof.

The invention also relates to compounds wherein R$^1$ is

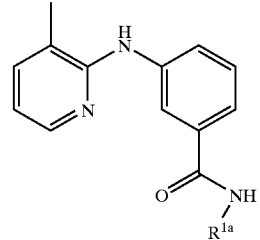

wherein R$^{1a}$ is selected from unsubstituted or substituted aryl, 5–6-membered heteroaryl and 9–10 membered fused heteroaryl,
  preferably phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, and benzthiazolyl;
wherein R$^{1a}$ is substituted with one or more substituents independently selected from halo, C$_{1-6}$-alkyl, optionally substituted C$_{3-6}$-cycloalkyl, optionally substituted phenyl, C$_{1-6}$-haloalkoxy, optionally substituted phenyloxy, benzyl, optionally substituted 5–6 membered heterocyclyl-C$_1$–C$_2$-alkylenyl, optionally substituted heteroaryl, optionally substituted heteroaryloxy, C$_{1-6}$-haloalkyl, and C$_{1-6}$-alkoxy;
  preferably wherein R$^{1a}$ is substituted with one or more substituents independently selected from chloro, fluoro, amino, hydroxy, cyclohexyl, phenylmethyl, morpholinylmethyl, ethyl, methylpiperdinylmethyl, methyl, propyl, isopropyl, butyl, tert-butyl, sec-butyl, isobutyl, methylpiperazinylmethyl, trifluoromethyl, phenyloxy, methoxy and ethoxy; and
wherein R$^2$ is selected from fluoro, chloro, bromo, NHR$^5$ and methyl optionally substituted with 1–3 substituents independently selected from phenyl, R$^9$, chloro, fluoro, OR$^5$, OC(O)R$^5$, —NR$^5$R$^5$ and COOR$^5$;
  preferably —NHR$^5$, fluoro, chloro, bromo, benzyl, trifluoromethyl, hydroxymethyl, methoxymethyl, aminomethyl and methyl;
wherein R$^4$ is selected from C$_1$–C$_4$ alkyl, optionally substituted phenyl, chloro, fluoro, hydroxy, methoxy and benzyl;
wherein R$^5$ is independently selected from H, C$_1$–C$_4$ alkyl, C$_2$–C$_4$ alkenyl, C$_2$–C$_4$ alkynyl; C$_3$–C$_6$ cycloalkyl, C$_4$–C$_6$ cycloalkenyl, phenyl optionally substituted with R$^4$, R$^9$, and C$_1$–C$_4$ alkyl substituted with 1–3 substituents independently selected from aryl, R$^7$ and R$^9$ groups;

preferably H, methyl and phenyl optionally substituted with chloro, fluoro, hydroxy, and methoxy; and
wherein $R^9$ is selected from 5–6-membered heteroaryl, and
wherein 0, 1, 2 or 3 atoms of each ring may be substituted by a substituent independently selected from $C_1$–$C_4$ alkyl, fluoro, chloro, trifluoromethyl, optionally substituted phenyl, hydroxy, methoxy, amino, methylamino, carboxy, methoxycarbonyl, formyl, methylcarbonyl, acetyl, and aminocarbonyl;

and pharmaceutically acceptable salts thereof.

The invention also relates to compounds of Formula II

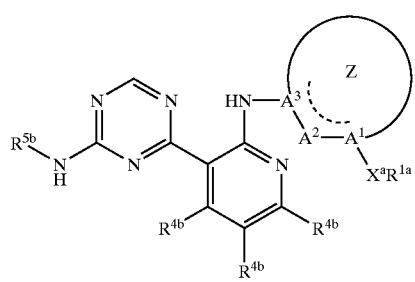

II wherein $A^1$, $A^2$ and $A^3$ are independently selected from C, CH, O, S, N and NH;
wherein ring Z is selected from
  a) 5- or 6-membered heteroaryl, preferably
    I) 5-membered heteroaryl selected from thienyl, furanyl, pyrrolyl, thiazolyl, oxazolyl, imidazolyl, pyrazolyl, isoxazolyl, triazolyl and isothiazolyl,
    even more preferably 5-membered heteroaryl selected from
  more specifically

A)

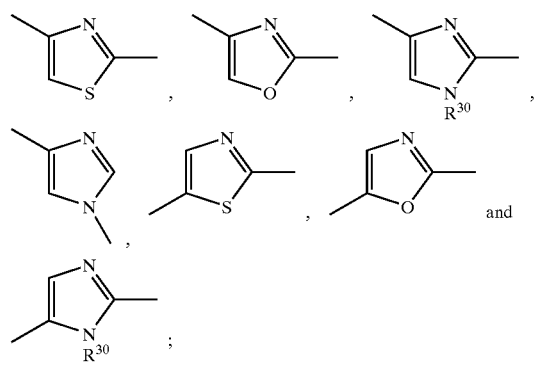

B)

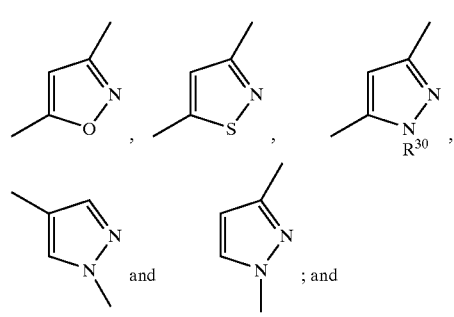

C)

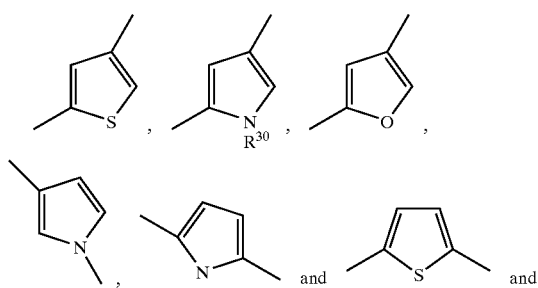

II) preferably 6-membered heteroaryl selected from pyridyl, pyrazinyl, pyrimidinyl, pyridazinyl, and triazinyl,
  even more preferably 6-membered heteroaryl selected from

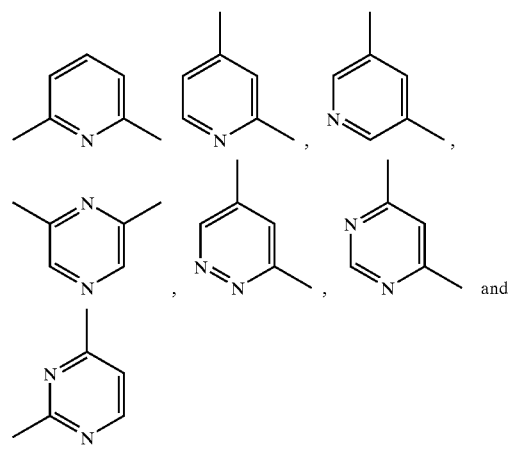

more specifically

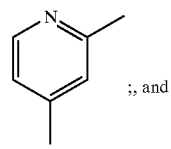

;, and b) phenyl,
  even more preferably

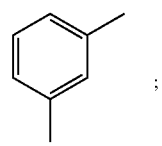

;

wherein $X^a$ is selected from

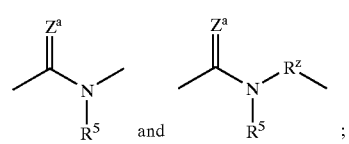

;

preferably $X^a$ is selected from

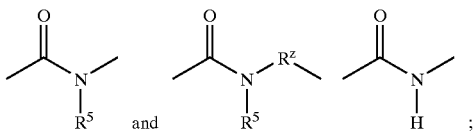

more preferably $X^1$ is
wherein $Z^a$ is oxygen or sulfur;
wherein $R^{1a}$ is selected from
a) substituted or unsubstituted 6–10 membered aryl,
preferably phenyl, naphthyl, indenyl, or tetrahydronaphthyl,
more preferably phenyl,
b) substituted or unsubstituted 5–6 membered heterocyclyl,
preferably 5–6 membered heteroaryl,
more preferably thienyl, pyridyl, pyrimidinyl, pyridazinyl, pyrazolyl, imidazolyl, oxazolyl, thiazolyl, thiadiazolyl, furyl, or pyrrolyl,
c) substituted or unsubstituted 9–10 membered fused heterocyclyl,
preferably 9–10 membered fused heteroaryl,
more preferably indazolyl, indolyl, benzothiadiazolyl, isoquinolyl, quinolyl, tetrahydroquinolyl, benzodioxanyl, or quinazolinyl;
d) cycloalkyl, and
e) cycloalkenyl;
wherein $R^{1a}$ is optionally substituted with one or more substituents independently selected from halo, —$OR^{15}$, —$SR^{15}$, —$CO_2R^{15}$, —$CONR^{15}R^{15}$, —$COR^{15}$, —$NR^{15}R^{15}$, —$NH(C_1-C_4$ alkylenyl$R^{15}$), —$SO_2R^{15}$, —$SO_2NR^{15}R^{15}$, —$NR^{15}C(O)OR^{15}$, —$NR^{15}C(O)R^{15}$, optionally substituted cycloalkyl, optionally substituted 5–6 membered heterocyclyl, optionally substituted phenyl, lower alkyl substituted with $R^4$, cyano, nitro, lower alkenyl and lower alkynyl;
preferably substituted with one or more substituents independently selected from halo, —$OR^{15}$, —$SR^{15}$, —$SO_2R^{15}$, —$CO_2R^{15}$, —$CONR^{15}R^{15}$, —$COR^{15}$, —$NR^{15}R^{15}$, —$NH(C_1-C_2$ alkylenyl$R^{15}$), —$(C_1-C_2$ alkylenyl)$NR^{15}R^{15}$, —$SO_2NR^{15}R^{15}$, —$NR^{15}C(O)OR^{15}$, —$NR^{15}C(O)R^{15}$, optionally substituted cycloalkyl, optionally substituted 5–6 membered heterocyclyl, optionally substituted phenyl, optionally substituted phenyl-$C_{1-2}$-alkylenyl, optionally substituted 5–6 membered heterocyclyl-$C_{1-2}$-alkylenyl, $C_{1-4}$-alkyl, cyano, $C_{1-4}$-hydroxyalkyl, nitro and $C_{1-2}$-haloalkyl;
more preferably $R^{1a}$ is unsubstituted or substituted with one or more substituents selected from chloro, fluoro, bromo, methoxy, phenyloxy, benzyl, methylthio, methyl, ethyl, propyl, butyl, isopropyl, isobutyl, sec-butyl, tert-butyl, trifluoromethyl, difluoromethyl, pentafluoroethyl, hydroxymethyl, cyano, carboxy, aminocarbonyl, methylcarbonyl, amino, methylamino, cyclopropyl, cyclohexyl, piperidinyl, morpholinyl, N-methylpiperazinyl, N-ethylpiperazinyl, morpholinylmethyl, methylpiperdinylmethyl, methylpiperazinylmethyl, methyl aminothiocarbonyl, N-methylaminomethylenyl, optionally substituted phenyl, N,N-diethylamino, and N,N-dimethylamino;
wherein $R^z$ is $C_1-C_4$ alkylenyl, where one of the $CH_2$ groups may be substituted with O or —NH—;
preferably $C_1-C_2$ alkylenyl, where one of the $CH_2$ groups may be substituted with O or —NH—;
more preferably —$CH_2CH_2$— or —$CH_2$—;
wherein $R^4$ and $R^{4b}$ are independently selected from H, $C_1-C_3$ alkyl, $C_2-C_3$ alkenyl, $C_2-C_3$ alkynyl, $C_3-C_6$ cycloalkyl, $C_4-C_6$ cycloalkenyl, phenyl, 5–6 membered heterocyclyl, halo, $CF_3$, $SR^5$, $OR^5$, $OC(O)R^5$, $NR^5R^5$, $COOR^5$, $NO_2$, CN, $C(O)R^5$, $C(O)NR^5R^5$, $S(O)_nR^5$, $S(O)_nNR^5R^5$, $NR^5C(O)R^5$, $NR^5(COOR^5)$, $NR^5S(O)_nR^5$, $OC(O)NR^5R^5$, $OS(O)_nNR^5R^5$, $NR^5S(O)_nOR^5$, $C_1-C_6$ alkyl substituted with 1–3 substituents independently selected from optionally substituted phenyl and optionally substituted 5–6 membered heterocyclyl, and
$C_2-C_6$ alkenyl substituted with 1–3 substituents independently selected from optionally substituted phenyl and optionally substituted 5–6 membered heterocyclyl;
preferably $R^4$ is selected from H, $C_1-C_3$ alkyl, $C_2-C_3$ alkenyl, $C_3-C_6$ cycloalkyl, phenyl, 5–6 membered heteroaryl, fluoro, chloro, $CF_3$, $SR^5$, $OR^5$, $OC(O)R^5$, $NR^5R^5$, $COOR^5$, $NO_2$, CN, $C(O)R^5$, $C(O)NR^5R^5$, $SO_2R^5$, $SO_2NR^5R^5$, $NR^5SO_2R^5$, and $C_1-C_6$ alkyl substituted with 1–3 substituents independently selected from optionally substituted phenyl and optionally substituted 5–6 membered heteroaryl;
more preferably H, methyl, phenyl, fluoro, chloro, $CF_3$, methoxy, methoxymethyl, acetyl, amino, methoxycarbonyl and benzyl;
wherein $R^{4b}$ is H;
wherein $R^5$ is selected from H, lower alkyl, phenyl and lower aralkyl;
preferably H, methyl and ethyl;
wherein $R^{5b}$ is independently selected from H, $C_1-C_4$ alkyl, phenyl optionally substituted with $R^4$, and
$C_1-C_4$ alkyl substituted with 1–3 substituents independently selected from $R^4$,
preferably H, $C_1-C_2$ alkyl, phenyl optionally substituted with $R^4$, and methyl substituted with 1–3 substituents independently selected from phenyl, fluoro, chloro, $CF_3$, methoxy, acetyl, amino, methoxycarbonyl, and
more preferably H, or methyl;
wherein $R^{15}$ is independently selected from H, lower alkyl, phenyl, 5–6 membered heterocyclyl, $C_3-C_6$ cycloalkyl, and lower haloalkyl;
preferably H, $C_{1-2}$-alkyl, phenyl, $C_3-C_6$ cycloalkyl, and $C_{1-2}$-haloalkyl;
wherein $R^{30}$ is selected from H, methyl, phenyl, and benzyl; and
wherein n is 0, 1 or 2;
and pharmaceutically acceptable salts thereof;
A family of specific compounds of particular interest within Formula I consists of compounds and pharmaceutically-acceptable salts thereof as follows:
3-[3-(4-Amino-[1,3,5]triazin-2-yl)-pyridin-2-ylamino]-N-(3-isopropyl-phenyl)-benzamide;
N-(4-phenoxyphenyl)-3-{1-[4-(3,4,5-trimethoxy-phenylamino)-[1,3,5]triazin-2-yl]-1H-benzimidazo-1-2-ylamino}benzamide;
N-(4-chlorophenyl)-3-{3-[4-(3,4,5-trimethoxy-phenylamino)-[1,3,5]triazin-2-yl]-pyridin-2-ylamino}-benzamide;
N-(phenyl)-3-{3-[4-(3,4,5-trimethoxy-phenylamino)-[1,3,5]triazin-2-yl]-pyridin-2-ylamino}benzamide;
N-(4-phenoxy-phenyl)-3-{3-[4-(3,4,5-trimethoxy-phenylamino)-[1,3,5]triazin-2-yl]-pyridin-2-ylamino}-benzamide; and
3-[3-(4-amino-[1,3,5]triazin-2-yl)-pyridin-2-ylamino]-N-(4-phenoxy-phenyl)benzamide.

Indications

Compounds of the present invention are useful for, but not limited to, the prevention or treatment of angiogenesis related diseases. The compounds of the invention have kinase inhibitory activity, such as VEGFR/KDR inhibitory activity. The compounds of the invention are useful in therapy as antineoplasia agents.

Compounds of the invention are useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

Preferably, the compounds are useful for the treatment of neoplasia selected from lung cancer, colon cancer and breast cancer.

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoictic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, pachydermoperiostosis and male infertility, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Thus the compounds are also useful for the treatment of vascular hyperpermeability.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, and the like. Hence, VEGF-mediated hyperpermeability can significantly contribute to disorders with these etiologic features. Thus the compounds of the present invention are useful in the treatment of VEGF-mediated hyperpermeability.

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, an inflammatory rheumatoid or rheumatic disease.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of diabetic conditions such as glaucoma, diabetic retinopathy and microangiopathy.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Definitions

The term "treatment" includes therapeutic treatment as well as prophylactic treatment (either preventing the onset of disorders altogether or delaying the onset of a preclinically evident stage of disorders in individuals). The term "prevention" includes either preventing the onset of disorders altogether or delaying the onset of a preclinically evident stage of disorders in individuals. This includes prophylactic treatment of those at risk of developing a disease, such as a cancer, for example. "Prophylaxis" is another term for prevention.

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by being therapeutically-effective in vivo.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyll" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals, having at least one carbon-carbon double bond, of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals, having at least one carbon-carbon triple bond, having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The terms "ring" and "ring system" refer to a ring comprising the delineated number of atoms, said atoms being carbon or, where indicated, a heteroatom such as nitrogen, oxygen or sulfur. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

Leaving groups are species that may be detached from a molecule during a reaction and are known in the art. Examples of such groups include, but are not limited to, halogen groups (e.g., I, Br, F, Cl), sulfonate groups (e.g., mesylate, tosylate), sulfide groups (e.g., $SCH_3$), and the like. Nucleophiles are species that may be attached to a molecule during reaction and are known in the art. Examples of such groups include, but are not limited to, amines, Grignard reagents, anionic species (e.g., alkoxides, amides, carbanions) and the like.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino.

The term "heterocyclyl" embraces saturated, partially saturated and unsaturated heteroatom-containing ring-shaped radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic group containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

The term "sulfonyl", whether used alone or linked to other terms such as alkylsulfonyl, denotes respectively divalent radicals —$SO_2$—.

The terms "carboxy" or "carboxyl", whether used alone or with other terms, such as "carboxyalkyl", denotes —$CO_2H$.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "heterocyclylalkylenyl" embraces heterocyclyl-substituted alkyl radicals. Preferable heterocyclyl alkylenyl radicals are "lower heterocyclylalkylenyl" radicals having heterocyclyl radicals attached to alkyl radicals having one to six carbon atoms. More preferred are heterocyclyl-$C_1$-$C_2$-alkylenyl radicals such as morpholinylmethyl, methylpiperdinylmethyl, methylpiperazinylmethyl, and the like.

The term "carbonyl", whether used alone or with other terms, such as "aminocarbonyl", denotes —(C=O)—.

The term "alkylamino" embraces "N-alkylamino" and "N,N-dialkylamino" where amino groups are substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino or the like.

The term "cycloalkyl" includes saturated carbocyclic groups. Preferred cycloalkyl groups include $C_3$–$C_6$ rings. More preferred compounds include, cyclopentyl, cyclopropyl, and cyclohexyl.

The term "cycloalkenyl" includes carbocyclic groups have one or more carbon-carbon double bonds. "Cycloalkenyl" and "cycloalkyldienyl" compounds are included. Preferred cycloalkenyl groups include $C_3$–$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The present invention preferably includes compounds that selectively inhibit KDR.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of KDR.

The present invention comprises a pharmaceutical composition comprising a therapeutically-effective amount of a compound of Formulas I–II in association with a least one pharmaceutically-acceptable carrier, adjuvant or diluent.

The present invention also comprises a method of treating angiogenesis related disorders, in a subject, the method comprising treating the subject having or susceptible to such disorder with a therapeutically-effective amount of a compound of the present invention.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with, or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku OF-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-l, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC$_{89}$-A1, Kyowa Hakko DC$_{92}$-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones,__ ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23–112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), SU 6668 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The invention relates to inhibitors of enzymes that catalyze phosphoryl transfer and/or that bind ATP/GTP nucleotides, compositions comprising the inhibitors, and methods of using the inhibitors and inhibitor compositions. The inhibitors and compositions comprising them are useful for treating or modulating disease in which phosphoryl transferases, including kinases, may be involved, symptoms of such disease, or the effect of other physiological events mediated by phosphoryl transferases, including kinases. The invention also provides for methods of making the inhibitor compounds and methods for treating diseases in which one or more phosphoryl transferase, including kinase, activities is involved.

Alternatively, the present compounds may also be used in co-therapies with other anti-neoplastic agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The present invention comprises a process for the preparation of a compound of Formula I–II.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Compounds of the present invention can possess, in general, tautomeric forms, which are included in the family of compounds in Formula I–II.

Also included in the family of compounds of Formula I–II are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–II may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are acetic, adipic, algenic, anthranilic, ascorbic, aspartic, benzoic, benzenesulfonic, butyric, camphoric, camphorsulfonic, citric, cyclopentanepropionic, cyclohexylaminosulfonic, digluconic, dodecylsulfonic, ethanesulfonic, formic, fumaric, galactaric, galacturonic, glycolic, gluconic, glucuronic, glucoheptanoic, glutamic, glycerophosphonic, heptanoic, hexanoic, 4-hydroxybenzoic, 2-hydroxyethanesulfonic, β-hydroxybutyric, lactic, malic, maleic, mandelic, mesylic, methanesulfonic, nicotinic, 2-naphthalenesulfonic, oxalic, palmoic, pectinic, pivalic, persulfuric, 2-phenylpropionic, picric, pyruvic, propionic, phenylacetic, embonic (pamoic), cyclopentane proprionic, pantothenic, toluenesulfonic, salicylic, sulfanilic, stearic, succinic, tartaric, thiocyanic, and undecanoic.

Suitable pharmaceutically-acceptable base addition salts of compounds of Formula I–II include metallic salts, such as salts made from alkali metals and alkaline earth metals including, for example, aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, ammonia, triethylamine, trimethylamine. All of these salts may be prepared by conventional means from the corresponding compound of the invention by reacting, for example, the appropriate acid or base with the compound of Formula I–II.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66, 1 (1977).

Combinations of substituents and variables envisioned by this invention are only those that result in the formation of stable compounds. The term "stable", as used herein, refers to compounds which possess stability sufficient to allow preparation.

As used herein, the compounds of this invention, including the compounds described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulas described herein.

Pharmaceutically acceptable salts of the compounds of this invention include those derived from pharmaceutically acceptable inorganic and organic acids and bases. Other acids, such as oxalic, while not in themselves pharmaceutically acceptable, may be employed in the preparation of salts useful as intermediates in obtaining the compounds of the invention and their pharmaceutically acceptable acid addition salts. This invention also envisions the quaternization of any basic nitrogen-containing groups of the compounds disclosed herein. Water or oil-soluble or dispersible products may be obtained by such quaternization.

The invention relates to a process for making a compound of any of the formulas described herein, comprising reacting a triazine of one or more of the formulas:

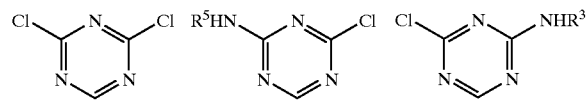

with an appropriate nucleophilic agent or agents, wherein the groups in said formulas are as defined herein.

In one embodiment, the invention relates to a process for making a compound of any of the formulas described herein, comprising reacting a triazine of one or more of the formulas:

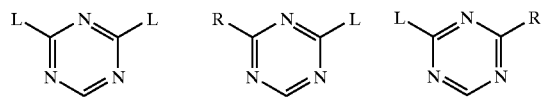

with an appropriate nucleophilic agent or agents, wherein L is defined as a leaving group and the groups in said formulas are as defined herein.

General Synthetic Procedures

The compounds of the invention can be synthesized according to the following procedures of Schemes 1–18, wherein the substituents are as defined for Formulas I–II, above, except where further noted.

Scheme 1

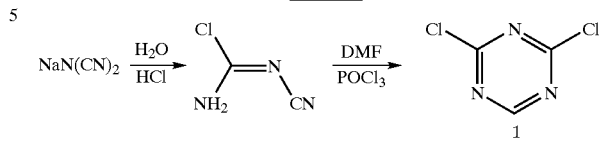

2,4-Dichloro-triazine 1 can be prepared according to the method set out in Scheme 1. Similar to that described by E. Allenstein, *Z. Anorg. Allgem. Chem,* 322, 265 (1963), sodium dicyanamide in water is reacted with concentrated HCl at a temperature of about −18–35° C. to give N-cyanochloroformamidine. N-Cyanochloroformamidine is added to a solution of DMF and POCl$_3$ in a solvent, such as CH$_2$Cl$_2$, preferably at a temperature about RT, to give 2,4-dichloro-1,3,5-triazine 1, similar to the method described by R. Harris, *Synthesis,* 11, 907, (1981).

Scheme 2

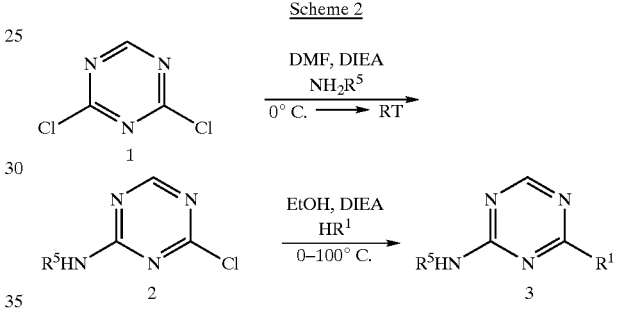

Monoamine substituted triazines 2 and di-substituted triazines 3 can be prepared according to the method set out in Scheme 2. 2,4-Dichloro-1,3,5-triazine 1 is coupled with amines, in the presence of base, such as DIEA, and a solvent, such as DMF, at a temperature of about 0° C. to about RT to give 4-chloro-[1,3,5]triazin-2-yl)amine 2.

Alternatively, 2,4-dichloro-1,3,5-triazine 1 is coupled with an amine in the presence of K$_2$CO$_3$, such as suspended in an organic solvent, such as AcCN, to yield triazines 2. Preferably the reaction is held at a temperature below RT, and more preferably at about 0° C.

Monoamine substituted triazines 2 are reacted with a heterocyclic group having an active hydrogen, such as an NH group, such as in solvent, such as IpOH, and in the presence of base, such as DIEA, to give the di-substituted triazine 3. Preferably the reaction is heated, more preferably at a temperature of about >75° C., even more preferably at a temperature of about 100° C. Alternatively, ethers, thioethers and the like can be prepared by substituting other nucleophiles for the amines described above.

Scheme 3

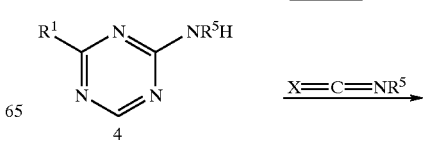

-continued

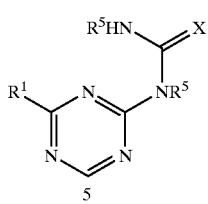
5

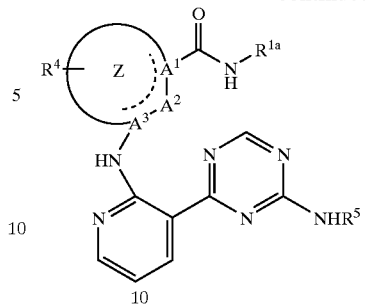
10

Ureas (X is O) or thioureas (X is S) 5 can be prepared according to the method set out in Scheme 3. Amines 4 are reacted with isocyanates or thioisocyantes to give the corresponding urea derivatives 5.

Cyclic amides can be prepared according to the method set out in Scheme 5. The amino group of compound 7 (where $R^o$ is alkyl, aryl, and the like) is protected, such as with Boc anhydride, followed by treatment to remove the ester, such as with base, forming the protected amine/free acid 8. Alternatively, other amino protecting groups known in the art can be used. Substituted amines are coupled with the free acid, such as with EDC, to form the protected amine/amide 9. The protected amine moiety is removed, such as with acid, and reacted with triazinyl-pyridinyl compounds to form the [([1,3,5]triazin-2-yl)-pyridin-2-ylamino]amide compounds 10. Preferably the amination is performed neat, and at a temperature between above about 50° C., and more preferably at about 90° C. to about 120° C.

Scheme 4

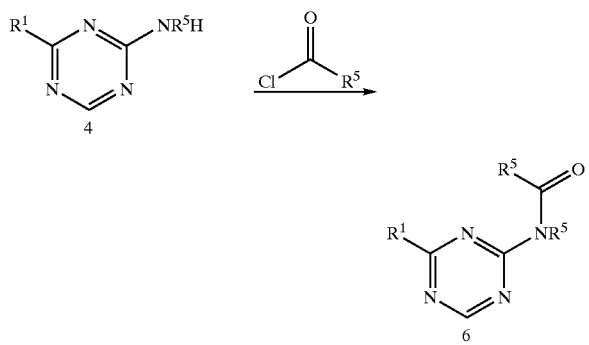

Amide substituted triazines 6 (where $R^5$ is not H) can be prepared according to the method set out in Scheme 4. Amines 4 are reacted with acylating reagents, such as acid halides, to give the corresponding amide derivatives 6.

Sceme 5

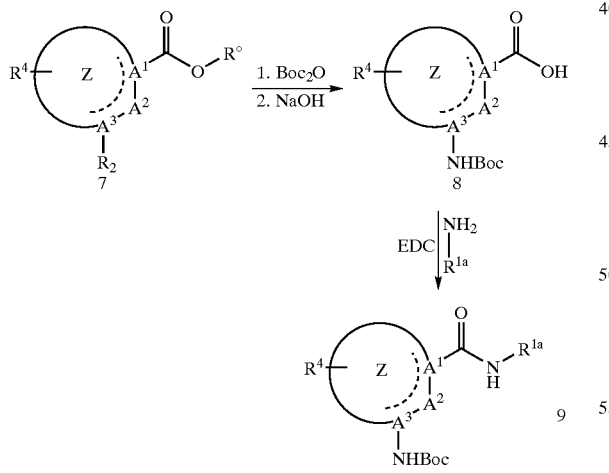

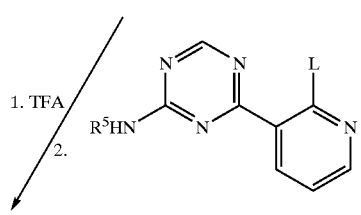

Scheme 6

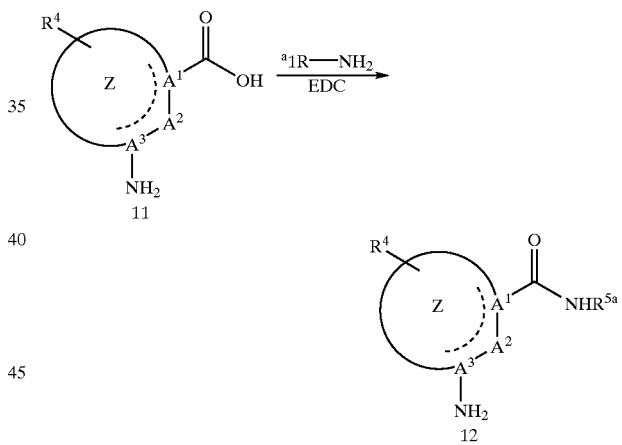

Alternatively, compounds 12 can be prepared from mixed acid/amines 11 as shown in Scheme 6. Substituted amines are coupled with the mixed acid/amines 11 such as with a coupling reagent, for example EDC, to form the mixed amine/amide 12.

Scheme 7

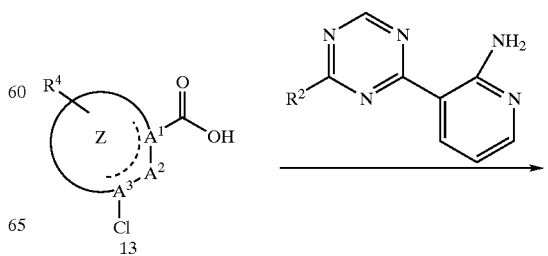

-continued

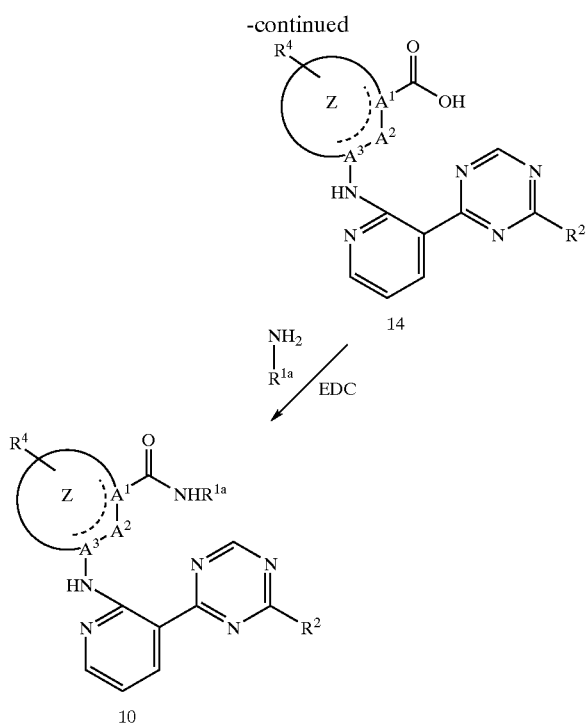

Substituted carboxamides 10 can be prepared from the corresponding halo analogs 13 by the process outlined in Scheme 7. Substituted amino acids 14 are prepared from the corresponding chloro compounds 13 such as by reacting with an amine at a suitable temperature, such as about 80° C. The acid 14 is coupled with an amine, preferably in the presence of a coupling agent such as EDC, to form the corresponding amide 10.

The amination process can be carried out as an Ullmann type reaction using a copper catalyst, such as copper[0] or a copper[I] compound such as copper[I]oxide, copper[I] bromide or copper[I]iodide in the presence of a suitable base (such as a metal carbonate, for example $K_2CO_3$) to neutralize the acid generated in the reaction. This reaction is reviewed in Houben-Weyl "Methoden der Organischen Chemie", Band 11/1, page 32–33, 1958, in Organic Reactions, Volume 14, page 19–24, 1965 and by J. Lindley (1984) in Tetrahedron, Volume 40, page 1433–1456. The amount of catalyst is typically in the range of 1 to 20 mole percent. The reaction is carried out in an inert, aprotic solvent such as an ether (for example dimethoxyethane or dioxane) or an amide (for example DMF or N-methylpyrrolidone), under an inert atmosphere in the temperature range of 60–180° C.

An alternative amination process involves using a Group VIII element, where the metal core of the catalyst should be a zero-valent transition metal, such as palladium or nickel, which has the ability to undergo oxidative addition to the Aryl-Halogen bond. The zero valent state of the metal may be generated in situ from the M[II] state. The catalyst complexes may include chelating ligands, such as alkyl, aryl or heteroaryl derivatives of phoshines or biphosphines, imines or arsines. Preferred catalysts contain palladium or nickel. Examples of such catalysts include palladium[II] chloride, palladium[II]acetate, tetrakis(triphenyl-phosphine) palladium[0] and nickel[II]acetylacetonate. The metal catalyst is typically in the range of 0.1 to 10 mole percent. The chelating ligands may be either monodentate, as in the case for example of trialkyphosphines, such as tributylphosphine, triarylphosphines, such as tri-(ortho-tolyl)phosphine, and triheteroaryl phosphines, such as tri-2-furylphosphine; or they may be bidentate such as in the case of 2,2'-bis(diphenylphosphino)-1,1'binaphthyl, 1,2-bis(diphenylphosphino)ethane, 1,1'-bis(diphenylphosphino)ferrocene and 1-(N,N-dimethyl-amino)-1'-(dicyclohexylphosphino)biphenyl. The supporting ligand may be complexed to the metal center prior to being added in the form of a metal complex to the reaction mixture or may be added to the reaction mixture as a separate compound. The supporting ligand is typically present in the range 0.01 to 20 mole percent. It is often necessary to add a suitable base to the reaction mixture, such as a trialkylamine (for example DIEA or 1,5-diazabicyclo[5,4,0]undec-5-ene), a Group I alkali metal alkoxide (for example potassium tert-butoxide) or carbonate (for example cesium carbonate) or potassium phosphate. The reaction is typically carried out in an inert aprotic solvent such as an ether (for example dimethoxyethane or dioxane) or an amide (for example DMF or N-methylpyrrolidone), under an inert atmosphere in the temperature range of about 60 to about 180° C.

The amination is preferably carried out in an inert, aprotic, preferably anhydrous, solvent or solvent mixture, for example in a carboxylic acid amide, for example DMF or dimethylacetamide, a cyclic ether, for example THF or dioxane, or a nitrile, for example AcCN, or in a mixture thereof, at an appropriate temperature, for example in a temperature range of from about 40° C. to about 180° C., and if necessary under an inert gas atmosphere, for example a nitrogen or argon atmosphere.

Scheme 8

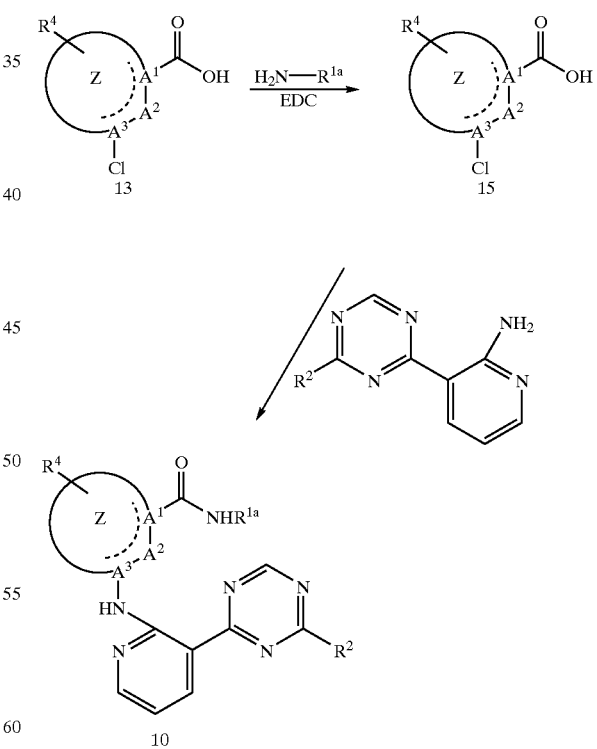

Substituted carboxamides 10 can be prepared from the corresponding halo analogs 13 by the process outlined in Scheme 8. The chloro acid 13 is coupled with an amine, preferably in the presence of a coupling agent such as EDC, to form the corresponding chloro amide 15. Substituted amino-amides 10 are prepared from the corresponding chloro compounds 15 such as by reacting with an amine at a suitable temperature, such as about 80° C. The amination reaction can be run in the presence of an appropriate catalyst such as a palladium catalyst, in the presence of an aprotic base such as sodium t-butoxide or cesium carbonate, or a nickel catalyst, or a copper catalyst.

outlined in Scheme 9. Trhe bromo/chloro acid 16 is coupled with an amine, preferably in the presence of a coupling agent such as EDC, to form the corresponding bromo substituted amide 17. Suzuki coupling with the bromo amide 17 and suitable boronic acids provides the substituted amide 15. Substituted amino-amides 10 are prepared from the corresponding chloro compounds 15 as described in Scheme 6.

Scheme 9

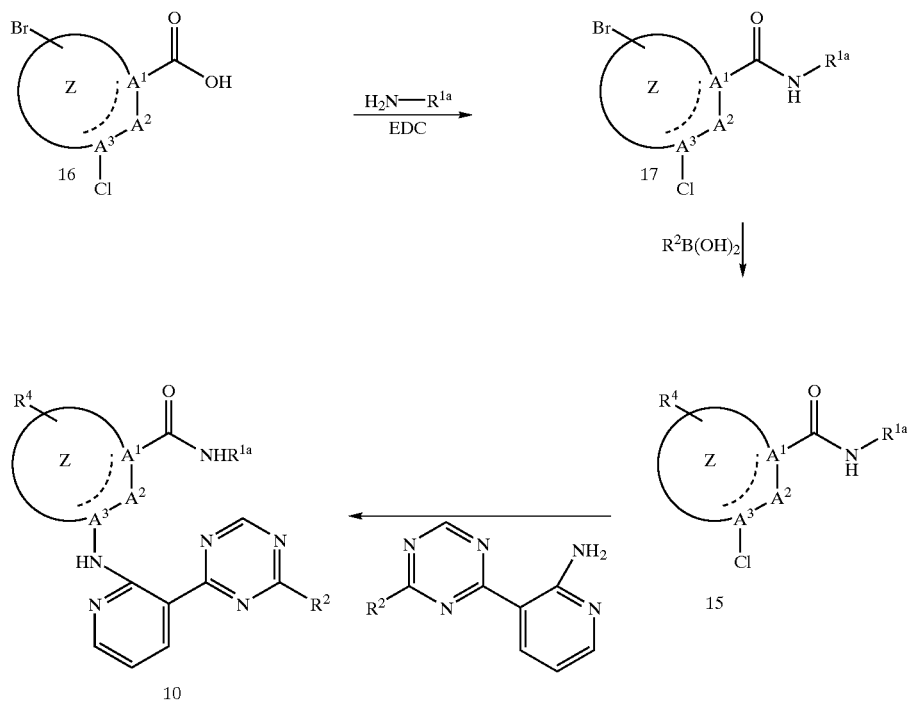

Substituted carboxamides 10 can be prepared from the corresponding bromo/chioro analogs 16 by the process Scheme 10

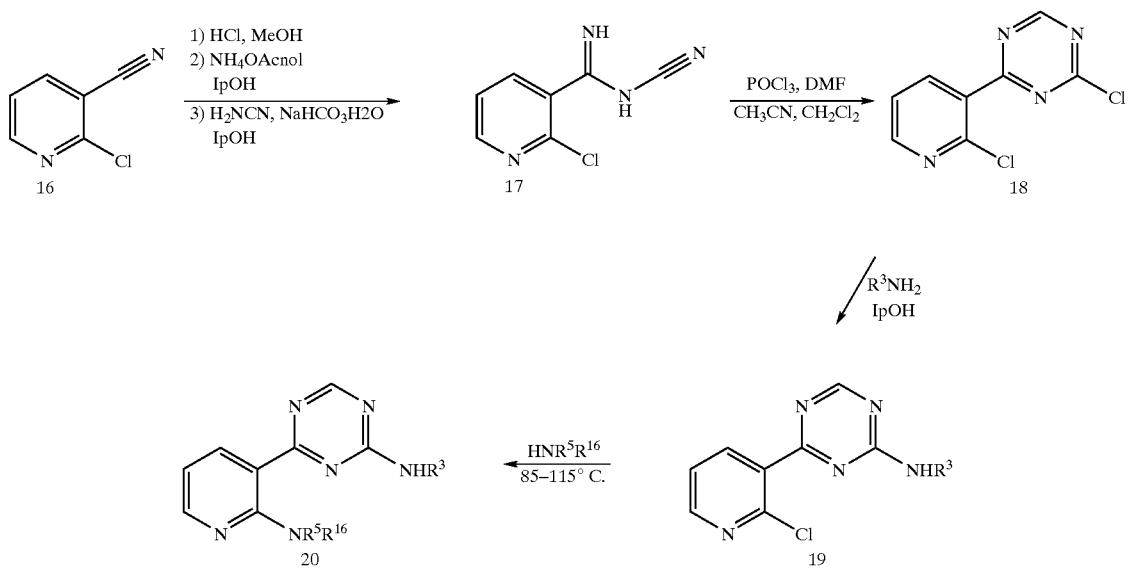

Substituted pyridyltriazines 18, 19 and 20 can be prepared from the corresponding cyanopyridine analogs 16 by the process outlined in Scheme 10. For example, 2-chloronicotinonitrile 16 is reacted with HCl in the presence of a dry alcohol, preferably at a temperature below RT. Ammonium acetate is added to form the amidine which is reacted with cyanamide in the presence of aqueous base, such as of 5% aqueous NaHCO$_3$ to form the cyanoamidine 17. Similar to the methodology of Scheme 3, cyanoamidine 17 is converted to the 2-chloro-[1,3,5]triazine 18 by reacting with POCl$_3$ and in a solvent such as DMF, preferably at about RT. 2-Chloro-4-(2-chloropyrid-3-yl)-[1,3,5]triazine 18 reacts with an optionally substituted amine (where R$^5$ is as defined in the formulas herein) to produce 2-amino-4-(2-chloropyrid-3-yl)-triazines 19. The remaining chloride may then be displaced by reaction with amine (neat or in a small amount of solvent) at an elevated temperature to form the 2-amino-4-(2-aminopyrid-3-yl)-triazines 20.

amine (neat or in a small amount of solvent) at an elevated temperature to form the 2-heterocyclic triazines 25.

Scheme 12

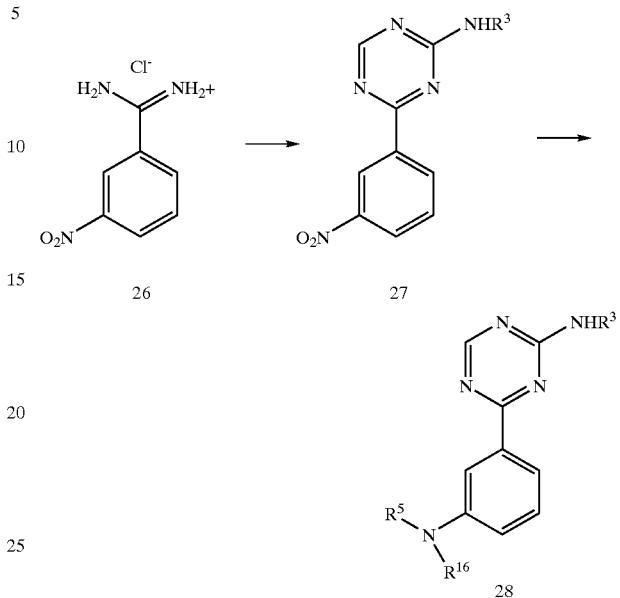

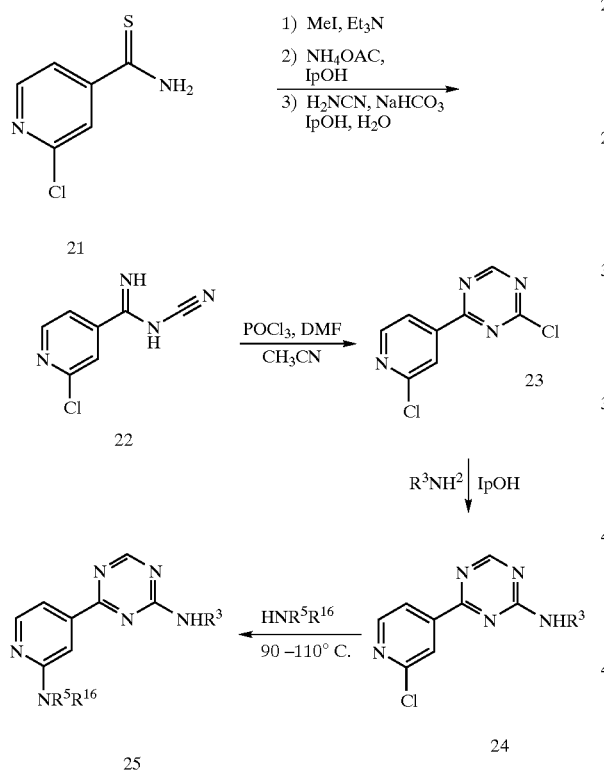

With use of the general procedure outlined in Schemes 1–11, 3-nitroamidines provide entry to a variety of aryl substitutions. Reduction of the nitroarene to the amine may be followed, for example, by acylation, reductive amination, sulfonylation, or urea formation to provide compounds exemplified above with independent R$^3$, R$^5$, and R$^{16}$ as defined in the formulas herein.

Scheme 13

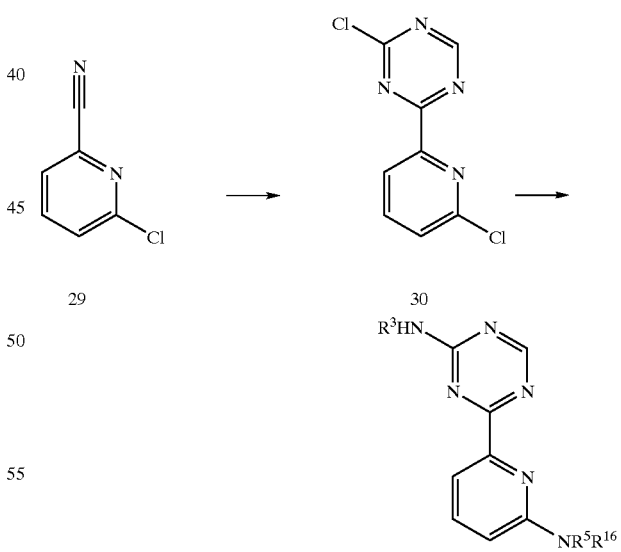

Substituted pyridyltriazines 23, 24 and 25 can be prepared from the corresponding pyridyl thioamides 21 by the process outlined in Scheme 11. For example, the thioamide of 2-chloroisonicotinamide [prepared according to Libermann, et al. *Memoires Presentes a la Societe Chimigue* 1958, 694–702] is alkylated, such as with methyl iodide. The resulting thioimidate salt is reacted with ammonium acetate in an alcohol, such as in IpOH to provide the amidine. This material is reacted with H$_2$NCN in the presence of base, such as NaHCO$_3$, and a solvent containing an alcohol such as IpOH, and H$_2$O, to obtain the cyanoamidine 22. This material is converted to the 2-chloro-[1,3,5]triazine 23 by reacting with POCl$_3$ and DMF at a temperature at RT or below RT. The 2-chloro-[1,3,5]triazine 23 reacts with an optionally substituted amine (where R$^5$ is as defined in the formulas herein) to produce 2-heterocyclic triazines 24. The remaining chloride may then be displaced by reaction with amine (neat or in a small amount of solvent) at an elevated temperature to form the 2-heterocyclic triazines 25.

With use of the general procedure outlined in Schemes 1–11, 6-chloro-pyridine-2-carbonitrile [Elman, B. *Tetrahedron*, 1985, 41, 4941–4948] may be functionalized to provide the pyridinyl[1,3,5] triazinylamines exemplified above with independent R$^3$, R$^5$ and R$^{16}$ as defined in the formulas herein.

Scheme 14

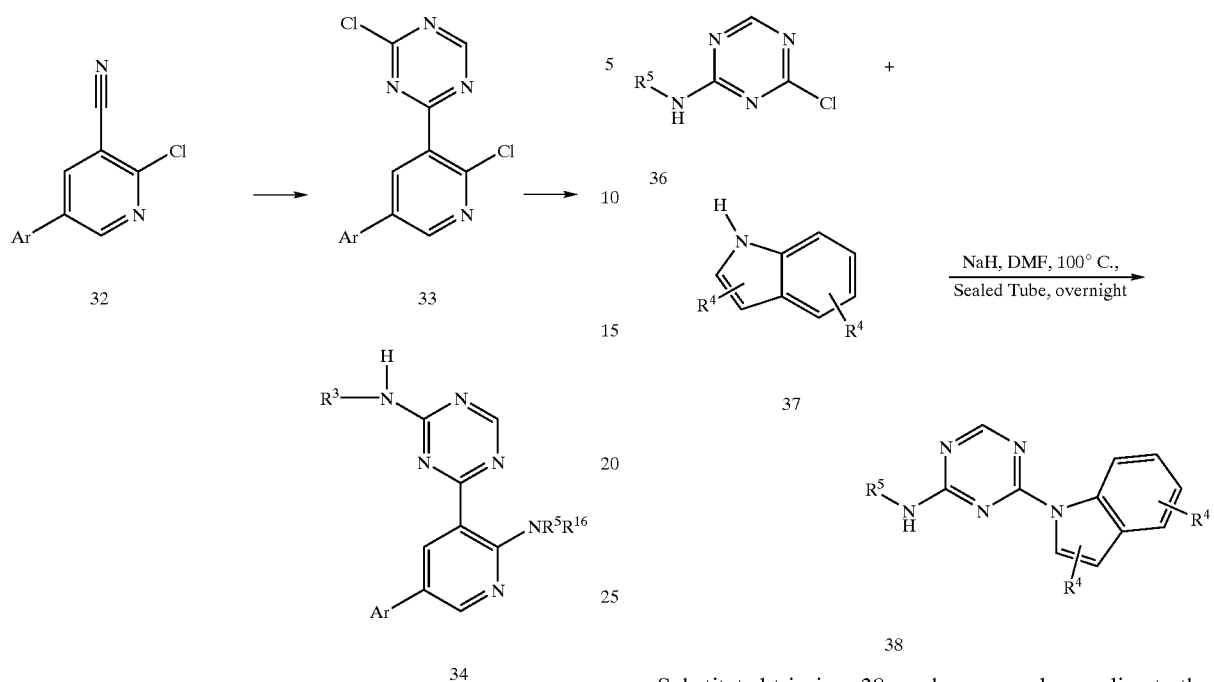

With use of the general procedure outlined in Schemes 1–11, 2-chloro-4-aryl-3-pyridine-carbonitriles [Church, R.; Trust, R.; Albright, J. D.; Powell, D. W. *J. Org. Chem.* 1995, 60, 3750–3758] may be functionalized to provide the pyridinyl[1,3,5]-triazinylamines exemplified above with independent $R^3$, $R^5$ and $R^{16}$ as defined in the formulas herein.

Scheme 15

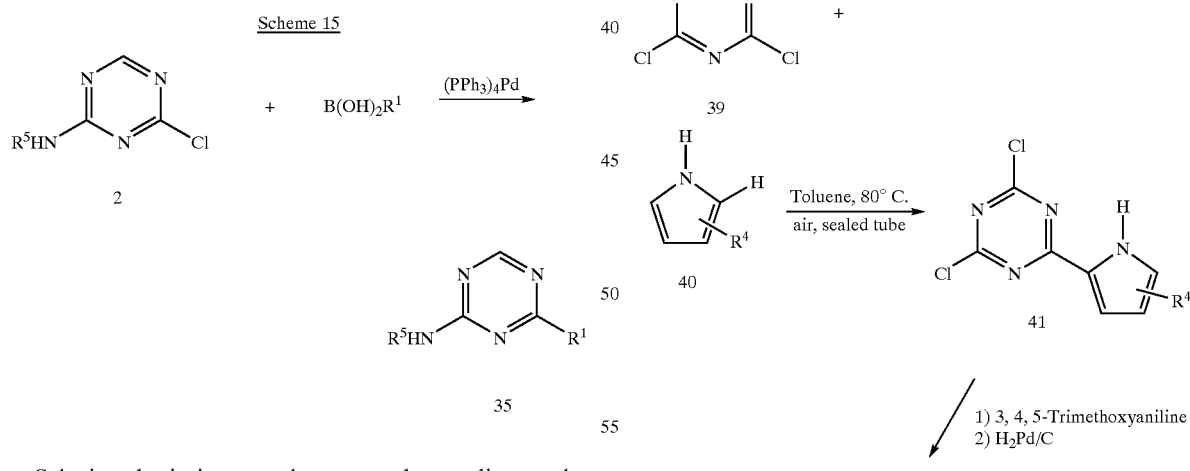

Substituted triazines can be prepared according to the method set out in Scheme 15, similar to that described by M. J. Sharp, et al. *Tetrahedron Letters,* 1987, 28, 5093–5096. Monoamine substituted triazines 2 are reacted with substituted boronic acids such as in the presence of tetrakis(triphenylphosphine) palladium(0), in an appropriate organic solvent, such as EtOH, to yield the disubstituted triazine 35. Preferably the reaction is heated to above RT, more preferably to a temperature where the solvent is at reflux.

Scheme 16

Substituted triazines 38 can be prepared according to the method set out in Scheme 16. Substituted indoles 37 in an appropriate solvent, such as DMF, is reacted with NaH (producing a strong gas evolution). This mixture is reacted with a chlorotriazine 36, such as at an elevated temperature, preferably about 100° C., forming the desired triazine 38.

Scheme 17

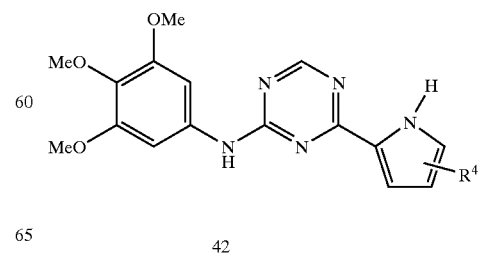

Substituted triazines can be prepared according to the method set out in Scheme 17, similar to that described by Chakrabarti and Tupper, *J. of Het. Chem.*, 1974, 11, 417–421. Cyanuric chloride is dissolved in a solvent, such as toluene. Pyrrole is added, the tube is sealed, and the reaction heated at a temperature above RT, preferably above about 50° C., more preferably at about 80° C. This gives the dichloride intermediate compound 41. Displacement of the chloride with an appropriate amine under standard conditions, followed by reduction of the remaining chloride by hydrogenation under standard conditions results in the desired product 42.

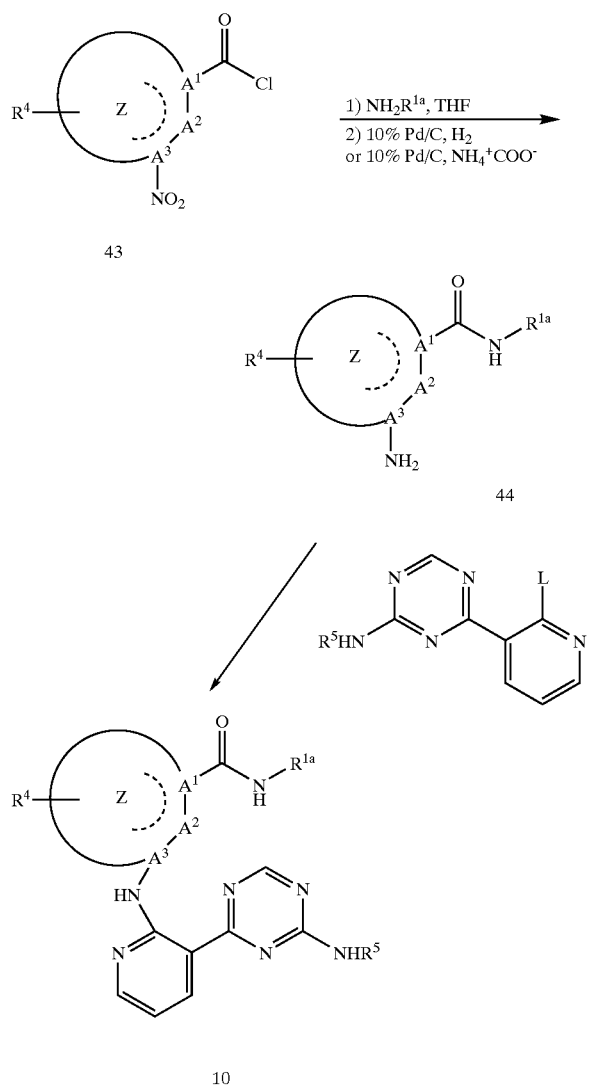

Cyclic amides can be prepared according to the method set out in Scheme 18. The nitro acid halide 43 is aminated, followed by reduction of the nitro group to form the amine/amide 44. Substituted amine/amide 44 are coupled with the triazinyl-pyridinyl compounds to form the [([1,3,5]triazin-2-yl)-pyridin-2-ylamino]amide compounds 10.

The starting compounds defined in Schemes 1–18 may also be present with functional groups in protected form if necessary and/or in the form of salts, provided a salt-forming group is present and the reaction in salt form is possible. If so desired, one compound of formula I can be converted into another compound of formula I or a N-oxide thereof; a compound of formula I can be converted into a salt; a salt of a compound of formula I can be converted into the free compound or another salt; and/or a mixture of isomeric compounds of formula I can be separated into the individual isomers.

N-Oxides can be obtained in a known matter by reacting a compound of formula I with hydrogen peroxide or a peracid, e.g. 3-chloroperoxy-benzoic acid, in an inert solvent, e.g. $CH_2Cl_2$, at a temperature between about −10 to about 35° C., such as about 0° C. to about RT.

If one or more other functional groups, for example carboxy, hydroxy, amino, or mercapto, are or need to be protected in a compound of Formulas I–II, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from about 130 to about 170° C., one molecule of the acid being expelled per molecule of a compound of formula I.

Salts can usually be converted to free compounds, e.g. by treating with suitable basic agents, for example with alkali metal carbonates, alkali metal hydrogen carbonates, or alkali metal hydroxides, typically $K_2CO_3$ or NaOH.

A compound of formula I, wherein $X^a$ is oxygen, can be converted into the respective compound wherein $X^a$ is sulfur, for example, by using an appropriate sulfur compound, e. g. using reaction with Lawesson's reagent (2,4-bis-(4-methoxyphenyl)2,4-dithioxo-1,2,3,4-dithiaphosphetan) in a halogenated carbon hydrate, such as $CH_2Cl_2$, or an aprotic solvent, such as toluene or xylene, at temperatures from about 30° C. to reflux.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the $H^+$ form, depending on the type of reaction and/or reactants at reduced, normal, or elevated temperature, for example in the range from about –100° C. to about 190° C., preferably from about –80° C. to about 150° C., for example at about –80 to about 60° C., at RT, at about –20 to about 40° C. or at the boiling point of the solvent used, under atmospheric pressure or in a closed vessel, where appropriate under pressure, and/or in an inert atmosphere, for example, under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include, for example, water, esters, typically lower alkyl-lower alkanoates, e.g EtOAc, ethers, typically aliphatic ethers, e.g. $Et_2O$, or cyclic ethers, e.g. THF, liquid aromatic hydrocarbons, typically benzene or toluene, alcohols, typically MeOH, EtOH, IpOH or 1-propanol, nitrites, typically AcCN, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. HOAc, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formula I–II, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

The following examples contain detailed descriptions of the methods of preparation of compounds of Formulas I–II. These detailed descriptions fall within the scope, and serve to exemplify, the above described General Synthetic Procedures which form part of the invention. These detailed descriptions are presented for illustrative purposes only and are not intended as a restriction on the scope of the invention.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention. The compounds of this invention may also be represented in multiple tautomeric forms, for example, as illustrated below:

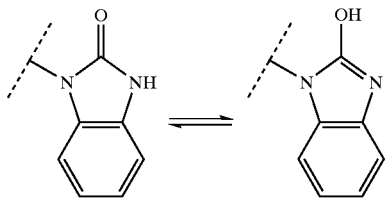

The invention expressly includes all tautomeric forms of the compounds described herein. The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necesssary. The processes may further comprise use of appropriate reaction conditions, including inert solvents, additional reagents, such as bases (e.g., LDA, DIEA, pyridine, K$_2$CO$_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB"), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Unless otherwise noted, all materials were obtained from commercial suppliers and used without further purification. All reactions involving air- or moisture-sensitive compounds were performed under a nitrogen atmosphere. All parts are by weight and temperatures are in Degrees centigrade unless otherwise indicated. All compounds showed NMR spectra consistent with their assigned structures.

In order that the invention described herein may be more readily understood, the following examples are set forth. It should be understood that these examples are for illustrative purposes only and are not to be construed as limiting this invention in any manner.

Analytical Methods

Unless otherwise indicated all HPLC analyses are run on a HP-1050 system with an HP Zorbax SB-C$_{18}$ (5□) reverse phase column (4.6×150 mm) run at 30° C. with a flow rate of 1.00 ml/min. The mobile phase used solvent A (H$_2$O/0.1% TFA) and solvent B (AcCN/0.1% TFA) with a 20 min gradient from 10% to 90% AcCN. The gradient is followed by a 2 min return to 10% AcCN and a 3 min flush. The peaks of interest eluted on the LC profiles at the times indicated.

LC-MS Method for:

Method A

1. Samples are run on a HP-1100 MSD system with a HP Zorbax SB-C$_8$ (5□) reverse phase column (4.6×50 mm) run at 30° C. with a flow rate of 0.75 ml/min.
2. The mobile phase used solvent A (H$_2$O/0% HOAc) and solvent B (AcCN/0.1% HOAc) with a 10 min gradient from 10% to 90% AcCN. The gradient is followed by a 1 min return to 10% AcCN and a 2 min flush.
3. The peaks of interest eluted on the LC profiles at the times indicated.

Method B

1. Samples are run on an HP-1100 system with an HP Zorbax SB-C$_8$ (5□) reverse phase column (4.6×50 mm) run at 30° C. with a flow rate of 1.5 ml/min.
2. The mobile phase used solvent A (H$_2$O/0.1% HOAc) and solvent B (AcCN/0.1% HOAc) with a 5 min gradient from 10% to 90% ACCN. The gradient is followed by a 0.5 min return to 10% ACCN and a 1.5 min flush.
3. The peaks of interest eluted on the LC profiles at the times indicated.

Preparative HPLC: Where indicated, compounds of interest were purified via preparative HPLC using a Gilson workstation with a 20×50 mm column at 20 ml/min. The mobile phase used solvent A (H$_2$O/0% TFA) and solvent B (AcCN/0.1% TFA) with a 10 min gradient from 5% to 100% AcCN. The gradient is followed by a 2 min return to 5% AcCN.

Proton NMR Spectra: Unless otherwise indicated, all $^1$H NMR spectra are run on a Varian series Mercury 300 MHz instrument. All observed protons are reported as parts-per-million (ppm) downfield from tetramethylsilane (TMS) or other internal reference in the appropriate solvent indicated.

The following abbreviations are used:

| | |
|---|---|
| RT | room temperature |
| H$_2$O | water |
| Na$_2$SO$_4$ | sodium sulfate |
| NaHCO$_3$ | sodium bicarbonate |
| tBuOMe | tert-butylmethoxide |
| DIEA | diisopropylethylamine |
| Et$_3$N | triethylamine |
| EDC | 1-(3-dimethylaminopropyl)-3-ethylcarbodiimide hydrochloride |
| DMSO | dimethylsulfoxide |
| BSA | bovine serum albumin |
| ATP | adenosine triphosphate |
| DTT | dithiothreitol |
| NaOH | sodium hydroxide |
| mg | milligram |
| g | gram |
| ml | milliliter |
| h | hour |
| AcCN | acetonitrile |
| THF | tetrahydrofuran |
| MeOH | methanol |
| EtOH | ethanol |
| IpOH | isopropanol |
| HOAc | acetic acid |
| EtOAc | ethyl acetate |
| Et$_2$O | ethyl ether |
| TFA | trifluoroacetic acid |
| DMF | dimethylformamide |
| POCl$_3$ | phosphoryl chloride |
| CH$_2$Cl$_2$ | dichloromethane |
| HCl | hydrochloric acid |
| NH$_4$Cl | ammonium chloride |
| Boc | tert-butyloxycarbonyl |
| HOBt | hydroxybenzotriazole |
| K$_2$CO$_3$ | potassium carbonate |
| min | minutes |
| MeI | methyl iodide |
| NaH | sodium hydride |
| LDA | lithium diisopropylamide |

Preparation I

Sodium dicyanamide (105.9 g, 1.19 mol) was nearly dissolved into H$_2$O and added quickly to concentrated HCl (530 ml) pre-cooled to about −18° C. The resulting slurry was stirred at −18° C. for about 15 min, warmed to 35° C. and re-cooled to 10° C. The resulting white precipitate was filtered, washed with small amounts of H$_2$O, and dried under vacuum for 20 h. N-Cyanochloroformamidine (~50 g) was obtained. DMF (27.3 ml) was dissolved in $CH_2Cl_2$ (550 ml) at RT. $POCl_3$ (27.3 ml) was added and after about 5 min, N-cyanochloroformamidine (30 g) was also added. The mixture was stirred overnight at RT, then washed 3 times with $H_2O$ and once with brine. The organic layer was dried over $Na_2SO_4$, filtered, and evaporated under reduced pressure. The white solid thus obtained was identified as the 2,4-dichloro-1,3,5-triazine.

Preparation II 2,4-Dichloro-1,3,5-triazine (1.054 g, 7.028 mmol) was dissolved in DMF (5 ml) and cooled to 0° C. To this solution, DIEA (1.225 ml, 7.028 mmol) and 3,4,5-trimethoxyaniline (1.185 g, 6.47 mmol) were added. The reaction mixture was kept at 0° C. for 15 to 30 min and at RT for 2 h. The reaction mixture was diluted with EtOAc and washed with brine. The organic layer was dried over $Na_2SO_4$, filtered, and evaporated in vacuo. The residue was added to $CH_2Cl_2$ and the resulting white precipitate was filtered and dried under reduced pressure to give (4-chloro-[1,3,5]triazin-2-yl)-(3,4,5-trimethoxy-phenyl)amine: MS m/z=279 $[M-Cl+OH_2]^+$. Calc'd for $C_{12}H_{13}ClN_4O_3$: 296.

Similarly, (3-chloro-4-fluoro-phenyl)-(4-chloro-[1,3,5]triazin-2-yl)-amine was prepared by reacting 2,4-dichlorotriazine with 3-chloro-4-fluoro-phenylamine.

1-(4-Chloro-[1,3,5]triazin-2-yl)-1H-benzoimidazol-2-ylamine was prepared according to the above method, substituting the appropriate amines, as a light yellow solid: MS m/z=246 $[M+H]^+$. Calc'd for $C_{10}H_7ClN_6$: 246.04.

Preparation III

To a solution of 5-nitroindazole (10 g, 61.3 mmol) in DMF (100 mL) was added $K_2CO_3$ (12.7 g, 91.9 mmol) and $PhCH_2Br$ (7.29 mL, 61.3 mmol). The resulting mixture was stirred at RT for 3.5 days, then poured into 400 mL of $H_2O$. The resulting slurry was filtered, rinsed once with water and dried in vacuo giving a beige solid. A portion of this crude material (2.5 g) was purified by chromatography ($SiO_2$, elution with 1:2 EtOAc-hexanes) giving 1-benzyl-5-nitro-1H-indazole and 2-benzyl-5-nitro-1H-indazole.

Preparation IV

To 1-benzyl-1H-indazol-5-ylamine (906.4 mg (3.58 mmol)) in MeOH (20 mL) and EtOAc (5 mL) at RT was added a slurry of 150 mg of 10% Pd-C in MeOH (5 mL). The resulting slurry was stirred under a balloon of $H_2$ for 1.2 h, filtered through Celite®, and rinsed with MeOH and EtOAc. Concentration of the filtrate gave 1-benzyl-1H-indazol-5-ylamine as a pinkish solid: MS m/z=224 $[M+H]^+$. Calc'd for $C_{14}H_{13}N_3$: 223.11.

Preparation V

To 2,4-dichloro-1,2,5-triazine (526.1 mg, 3.51 mmol) in DMF (15 mL) at 0° C. was added DIEA (0.733 mL, 4.21 mmol). The resulting yellow solution was stirred at 0° C. for 20 min and 1-benzyl-1H-indazol-5-ylamine (783.5 mg, 3.51 mmol) was added in one portion followed by 2×2.5 mL DMF flask rinses. The resulting mixture was stirred at 0° C. for 30 min, at RT for 4.5 h, then diluted with EtOAc. The organic layer was washed twice with water and once with brine. The aqueous layer and washings were extracted with EtOAc. The combined organics were dried, concentrated, and purified by chromatography ($SiO_2$, elution with 1:1 EtOAc-hexanes) to give a slightly impure pinkish solid. Trituration with $Et_2O$ gave (1-benzyl-1H-indazol-5-yl)-(4-chloro-[1,3,5]triazin-2-yl)amine as a light pink solid: MS m/z=337 $[M+H]^+$. Calc'd for $C_{17}H_{13}ClN_6$: 336.09.

Preparation VI

To (1-benzyl-1H-indazol-5-yl)-(4-chloro-[1,3,5]triazin-2-yl)amine (473 mg, 1.40 mmol) in DMF (7.5 ml) at 0° C. was added MeI (0.262 mL, 4.21 mmol), followed by NaH (60% dispersion in oil)(67.4 mg, 1.69 mmol). The resulting mixture was stirred at 0° C. for 4.25 h. An additional 10 mg NaH was added after 3.1 h as TLC indicated remaining starting material. At this point, the reaction mixture was quenched with sat'd aq $NH_4Cl$ and diluted with water and EtOAc. The organic layer was washed with water and brine. The aqueous layer and washings were extracted once with EtOAc. The combined organics were dried, concentrated and purified by chromatography ($SiO_2$, elution with 1:1 EtOAc-hexanes) to give N-methyl-(1-benzyl-1H-indazol-5-yl)-(4-chloro-[1,3,5]triazin-2-yl)amine as a pale oil: MS m/z=351 $[M+H]^+$. Calc'd for $C_{18}H_{15}ClN_6$: 350.10.

Preparation VII (3-Amino-phenyl)-acetic acid methyl ester was prepared by reacting 3-aminophenylacetic acid with acetyl chloride in MeOH to afford the corresponding methyl ester, HCl salt, (3.09 g, 15.324 mmol). The ester was dissolved in DMF (5 ml) with DIEA (2.67 ml, 15.324 mmol) and cooled to 0° C. To this solution was added dropwise a 0° C. solution of DMF (5 ml) containing 2,4-dichloro-1,3,5-triazine (2.297 g, 15.324 mmol) and DIEA (2.67 ml, 15.324 mmol). The reaction was stirred at ODC for 15 min and then at RT for 1 h. The reaction mix was diluted with EtOAc and water. The layers were separated, and the aqueous layer was extracted twice with EtOAc. The combined organic layers were washed 4 times with brine and dried over $Na_2SO_4$. The crude was concentrated down and dried under reduced pressure, giving [3-(4-chloro-[1,3,5]triazin-2-ylamino)-phenyl]-acetic acid methyl ester (4.3 g, 100%).

Similarly, 3-(4-chloro-[1,3,5]triazin-2-ylamino)benzoic acid methyl ester was prepared.

Preparation VIII 2,4-Dichloro-1,3,5-triazine (173.7 mg, 1.158 mmol) was dissolved in DMF (1 ml). To the stirring solution, cooled to 0° C., was added DIEA (202 µl, 1.158 mmol). This solution was added dropwise to a 0° C. mix of DMF (1 ml) and 3-aminophenyl acetamide. The reaction was stirred at 0° C. for min and then at RT for 1 h. The reaction mix was diluted with EtOAc and water. The layers were separated, and the aqueous layer was extracted twice with EtOAc. The combined organic layer was washed 3 times with brine, dried over $Na_2SO_4$, and concentrated under reduced pressure, giving 2-[3-(4-chloro-[1,3,5]triazin-2-ylamino)-phenyl]acetamide.

Preparation IX

2-[3-(4-Chloro-[1,3,5]triazin-2-ylamino)-phenyl]-acetamide (136.5 mg, 0.5177 mmol) is combined with 2-chlorobenzimidazole (86.9 mg, 0.5177 mmol) and potassium carbonate (93 mg, 0.673 mmol) in AcCN (5 ml) and heated at 65–75° C. for 2 to 20 hours. The reaction mix is cooled to RT and the inorganic salts are filtered off. The AcCN solution is concentrated down under reduced pressure. The crude is purified on a silica gel column with an EtOAc/hexane to MeOH/$CH_2Cl_2$ elution gradient, giving 2-{3-[4-(2-chloro-benzimidazol-1-yl)-[1,3,5]triazin-2-ylamino]-phenyl}acetamide.

Preparation X

To a mixture of 2-[3-(4-chloro-[1,3,5]triazin-2-ylamino)-phenyl]acetamide (36.6 mg, 0.1388 mmol) in IpOH (1 ml) were added DIEA (27 µl, 0.1527 mmol) and 3-bromoaniline (26.3 mg, 0.1527 mmol). The mix was heated at 100–120° C. for 18 h. The solution was cooled to RT and sonicated. The precipitate was filtered and dried under reduced pressure, giving 2-{3-[4-(3-bromophenylamino)-[1,3,5]triazin-2-ylamino]-phenyl}acetamide.

Preparation XII 2,4-Dichloro-1,3,5-triazine (405.8 mg, 2.7065 mmol) is dissolved in DMF (2 ml). To the stirring solution cooled to 0° C. is added DIEA (471 µl, 2.7065 mmol). This solution is added dropwise to a 0° C. mix of DMF (2 ml) and 3-[1,2,3]triazol-1-ylmethyl-phenylamine (471.5 mg, 2.7065 mmol). The reaction is stirred at 0° C. for 15 minutes to 40 minutes and then at RT for 20 minutes to 2 hours. The mixture is diluted with EtOAc and water. The layers are separated, and the aqueous layer is extracted twice with EtOAc. The combined organic layer is washed 3 times with brine, dried over $Na_2SO_4$, and concentrated under reduced pressure, giving (4-chloro-[1,3,5]triazin-2-yl)-(3-[1,2,3]triazol-1-ylmethyl-phenyl)amine as a white foam.

Preparation XIII 2,4-Dichloro-1,3,5-triazine (327.5 mg, 2.1845 mmol) was dissolved in DMF (2 ml) and cooled to 0° C. To this solution were added DIEA (381 µl, 2.184 mmol) and 2-chloro-benzimidazole (333.3 g, 2.1845 mmol). The reaction mixture was kept at 0° C. for 15 min and then at RT for 45 min. The crude 2-chloro-1-(4-chloro-[1,3,5]triazin-2-yl)-1H-benzimidazole was used as is in the next step.

To crude 2-chloro-1-(4-chloro-[1,3,5]triazin-2-yl)-1H-benzimidazole was added DIEA (381 µl, 2.184 mmol) and then a solution of DMF (1 ml) and 3-(1H-tetrazol-5-ylmethyl)phenylamine (382.7 mg, 2.1845 mmol). The reaction was heated at 60–75° C. for 18 h. The reaction was cooled to RT and concentrated to a small volume. The crude was eluted on a silica gel column with a $MeOH/CH_2Cl_2$ elution gradient, giving [4-(2-chloro-benzimidazol-1-yl)-[1,3,5]triazin-2-yl]-[3-(1H-tetrazol-5-ylmethyl)-phenyl]amine.

Preparation XIV 2,4-Dichloro-1,3,5-triazine (204 mg, 1.362 mmol) is dissolved in DMF (2 mL) and cooled to 0° C. To this solution are added DIEA (238 µl, 1.362 mmol) and 3,5-dimethoxy-4-(2-[1,2,3]triazol-1-yl-ethoxy)phenylamine (360 mg, 1.362 mmol) dissolved in DMF (2 mL). (The aniline is prepared the following way: 2,6-dimethoxy-4-nitrophenol is prepared according to (Tepe, *Med. Chem.*, 39, (1996); 2188–2196) and reacted via Mitsunobu with 2-(1-triazolyl)ethanol (prepared according to Kume et al., *Journal of Antibiotics*; (1993) 46, 177–195). The Mitsunobu product is reduced to the aniline via Pd on carbon.) The mixture is kept at 0° C. for 15 to 30 minutes and then at RT for 15 minutes to 2 hours. The reaction mix is added to water, whereupon the compound precipitated out of solution. The precipitate is filtered and dried under vacuum, giving (4-chloro-[1,3,5]triazin-2-yl)-[3,5-dimethoxy-4-(2-[1,2,3]triazol-1-yl-ethoxy)phenyl]amine.

(4-Chloro-[1,3,5]triazin-2-yl)-[3,5-dimethoxy-4-(2-morpholin-4-yl-ethoxy)phenyl]amine and (4-chloro-[1,3,5]triazin-2-yl)-[3,4-dimethoxy-5-(morpholin-4-ylmethoxy)phenyl]amine were prepared in a similar fashion.

Preparation XV (4-Chloro-[1,3,5]triazin-2-yl)-[3,5-dimethoxy-4-(2-[1,2,3]triazol-1-yl-ethoxy)phenyl]amine (407 mg, 1.076 mmol) is combined with 2-chlorobenzimidazole (164 mg, 1.076 mmol) and $K_2CO_3$ (179 mg, 1.292 mmol) in AcCN (10 ml) and heated at 65 to 75° C. for 4 to 20 hours. The mix is concentrated down under reduced pressure and treated with water. A white precipitate forms which is filtered and dried under vacuum, giving [4-(2-chloro-benzimidazol-1-yl)-[1,3,5]triazin-2-yl]-[3,5-dimethoxy-4-(2-[1,2,3]triazol-1-yl-ethoxy)phenyl]-amine.

[4-(2-Chloro-benzimidazol-1-yl)-[1,3,5]triazin-2-yl]-[3,5-dimethoxy-4-(2-morphol-4yl-ethoxy)phenyl]amine and [4-(2-chloro-benzimidazol-1-yl)-[1,3,5]triazin-2-yl]-[3,4-dimethoxy-5-(2-morpholin-4-yl-ethoxy)phenyl]amine were prepared in a similar fashion.

Preparation XVI

[3-(4-Chloro-[1,3,5]triazin-2-ylamino)phenyl]acetic acid methyl ester (3.530 g, 12.67 mmol) is combined with 2-chlorobenzimidazole (1.933 g, 12.67 mmol) and $K_2CO_3$ (2.101 g, 15.20 mmol) in AcCN (50 ml) and heated at 65–750° C. for 2 to 20 hours. The reaction mix is cooled to RT. The inorganic salts are filtered off. The AcCN solution is concentrated down under reduced pressure. The crude is purified by chromatography with an EtOAc/hexane elution gradient, giving {3-[4-(2-chloro-benzimidazol-1-yl)-[1,3,5]triazin-2-ylamino]phenyl}acetic acid methyl ester.

Similarly, 4-[4-(2-chlorobenzimidazol-1-yl)-[1,3,5]triazin-2-ylamino]benzoic acid methyl ester was prepared. MS m/3=[M+H] is 381. Calc'd for $C_{18}H_{13}ClN_6O_2$: 380.08.

Preparation XVII (4-Chloro-[1,3,5]triazin-2-yl)-(3-[1,2,3]triazol-1-ylmethyl-phenyl)-amine (552.7 mg, 1.921 mmol) is combined with 2-chlorobenzimidazole (381 mg, 2.497 mmol) and $K_2CO_3$ (372 mg, 2.689 mmol) in AcCN (10 ml) and heated at 65–75° C. for 2 to 20 h. The reaction mix is cooled to RT and diluted with MeOH and $CH_2Cl_2$. The inorganic salts are filtered off and the organic solution is concentrated under reduced pressure. The crude is treated with AcCN (5–8 ml), forming a precipitate. The precipitate is filtered and dried, giving [4-(2-chloro-benzoimidazol-1-yl)-[1,3,5]triazin-2-yl]-(3-[1,2,3]triazol-1-ylmethyl-phenyl)-amine.

Similarly, [4-(2-chloro-imidazol-1-yl)-[1,3,5]triazin-2-yl]-(3,4,5-trimethoxy-phenyl)amine was prepared by reacting (4-chloro-[1,3,5]triazin-2-yl)-(3,4,5-trimethoxy-phenyl)-amine with 2-chloroimidazole (prepared according to literature procedure: "Facile Synthesis of 2-Substituted Imidazoles", K. L. Kirk, *J. Org. Chem.* 43 (1978) 4381–4383). MS m/z=363 $[M+H]^+$. Calc'd for $C_{15}H_{15}ClN_6O_3$: 362.09.

Preparation XVIII

To a mixture of (4-chloro-[1,3,5]triazin-2-yl)-(3-[1,2,3]triazol-1-ylmethyl-phenyl)-amine (64.8 mg, 0.2252 mmol) in IpOH (1 ml) were added DIEA (39 ul, 0.225 mmol) and 3-bromoaniline (38.7 mg, 0.2252 mmol). The mix was heated at 100–120° C. for 4 to 18 h. The solution was cooled to RT and sonicated. A precipitate formed, was filtered and dried under reduced pressure giving N-(3-bromophenyl)-N'-(3-[1,2,3]triazol-1-yl-methyl-phenyl)-[1,3,5]triazine-2,4-diamine.

Preparation XIX 2,4-Dichloro-1,3,5-triazine (122.7 mg, 0.8182 mmol) is dissolved in DMF (1 ml). To the stirred solution cooled to 0° C. is added DIEA (150 µl, 0.861 mmol). This solution is added dropwise to a 0° C. mix of DMF (2 ml), DIEA (150 µl, 0.861 mmol) and 3-(1-trityl-1H-imidazol-2-ylmethyl)-phenylamine (340 mg, 0.8182 mmol) (prepared from 3-nitrophenylacetonitrile to yield the imidazoline (Amemiya et al, *J. Med. Chem.*, (1992) 35, 750–755), which is oxidized to the imidazole (Amemiya et al.; *Synthetic Communications*, 20 2483–2489), trityl-protected and reduced from nitro to amine). The reaction is stirred at 0° C. for 15 minutes to 40 minutes and then at RT for 20 minutes to 2 h. The reaction mix is diluted with EtOAc and water. The layers are separated, and the aqueous layer is extracted twice with EtOAc. The combined organic layer is washed 3 times with brine, dried over $Na_2SO_4$, and concentrated under reduced pressure. The crude is eluted on a silica gel column with EtOAc/hexane (1:1), giving (4-chloro-[1,3,5]triazin-2-yl)-[3-(1-trityl-1H-imidazol-2-ylmethyl)phenyl]amine.

Preparation XX
(4-Chloro-[1,3,5]triazin-2-yl)-[3-(1-trityl-1H-imidazol-2-ylmethyl)phenyl]amine (331 mg, 0.6256 mmol) is combined with 2-chlorobenzimidazole (114.6 mg, 0.7508 mmol) and K$_2$CO$_3$ (190 mg, 1.376 mmol) in AcCN (5 ml) and heated at 65–75° C. for 2 to 20 h. The reaction mix is cooled to RT. The product precipitates out of AcCN, and is filtered off. The crude solid is treated with water, filtered and dried, giving [4-(2-chloro-benzoimidazol-1-yl)-[1,3,5]triazin-2-yl]-[3-(1-trityl-1H-imidazol-2-ylmethyl)phenyl]amine.

Preparation XXI
A mixture of the compound 2,4-dichloro-1,3,5-triazine (2.5 g, 16.7 mmol) and solid K$_2$CO$_3$ (6.9 g, 49.9 mmol) was suspended in AcCN (50 mL) under nitrogen at 0° C. followed by addition of N-methyl-3-chloroaniline (2.5 g, 17.7 mmol). The mixture was stirred at 0° C. for 2 h. The reaction was quenched by pouring onto ice/water. The white solid formed was collected by suction filtration and dried under vacuum to give N-methyl-2-chloro-4-(3-chloroanilino)-1,3,5-triazine. MS m/z=256. Calc'd for C$_{10}$H$_8$Cl$_2$N$_4$: 254.01.

Similarly, (3-chlorophenyl)-(4-chloro-[1,3,5]triazin-2-yl) amine was prepared from 3-chloroaniline and 2,4-dichloro-1,3,5-triazine.

Preparation XXII
To a mixture of (3-chloro-4-fluoro-phenyl)-(4-chloro-[1,3,5]triazin-2-yl)-amine (1.7 g, 6.56 mmol) and MeI (1.5 mL) in DMF (20 mL) under a nitrogen atmosphere was added NaH (60% dispersion, 0.53 mg, 13.3 mmol). The mixture was stirred for 3 h. The reaction was quenched by the addition of water and the organic extracts are taken up in EtOAc, dried over anh. MgSO$_4$ and concentrated under reduced pressure. The crude product was purified via medium pressure liquid chromatography using CH$_2$Cl$_2$ as the solvent system to give N-methyl-2-chloro-4-(3-chloro-4-fluoroanilino)-1,3,5-triazine.

Similarly, allyl-(3-chloro-4-fluoro-phenyl)-(4-chloro-[1,3,5]triazin-2-yl)-amine was prepared from allyl bromide and 2-chloro-4-(3-chloroanilino)-1,3,5-triazine. Similarly, N-ethyl-2-chloro-4-(3-chloro-4-fluoroanilino)-1,3,5-triazine is prepared from ethyl iodide and 2-chloro-4-(3-chloroanilino)-1,3,5-triazine.

Preparation XXIII
2,4-Dichloro-1,3,5-triazine (12.6 g, 84 mmol) was dissolved in DMF (100 mL) under N$_2$ and cooled to 0° C. DIEA (11.7 g, 90 mmol) was added, followed by 4-aminoveratrole (13.35 g, 87 mmol). The reaction solution was stirred with gradual warming to RT. The reaction was quenched after 3.5 h with water, which causes a gray precipitate to form. This precipitate was recovered by vacuum filtration, washed with cold water, dried under high vacuum, then eluted through a 28×4.5 cm column of silica gel (0.1% NH$_4$OH buffered 1%, 2%, 3%, 4%, and 5% MeOH/CH$_2$Cl$_2$ step gradient) giving (4-chloro-[1,3,5]triazin-2-yl)-(3,4-dimethoxy-phenyl)-amine as an off white solid.

Preparation XXIV
4-Chloro-[1,3,5]triazin-2-yl)-(3,4,5-trimethoxy-phenyl) amine (300 mg, 1 mmol) was dissolved in hydrazine monohydrate (0.63 mL, 20 mmol) and heated at 120° C. for 25 min. The resulting white solid was filtered and dried to provide (4-hydrazino-[1,3,5]triazin-2-yl)-(3,4,5-trimethoxy-phenyl)-amine. (4-Hydrazino-[1,3,5]triazin-2-yl)-(3,4,5-trimethoxy-phenyl)-amine (40 mg, 0.14 mmol) was reacted with benzoyl acetonitrile (20 mg, 0.14 mmol) in refluxing absolute EtOH (1 mL). The resulting [4-(5-amino-4-phenyl-pyrazol-1-yl)-[1,3,5]triazin-2-yl]-(3,4,5-trimethoxy-phenyl)-amine was purified by silica gel chromatography. MS m/z=442 [M+Na]$^+$. Calc'd for C$_{21}$H$_{21}$N$_7$O$_3$: 419.17.

The related regioisomer, [4-(5-amino-3-phenyl-pyrazol-1-yl)-[1,3,5]triazin-2-yl]-(3,4,5-trimethoxy-phenyl)-amine, was prepared as above by using formyl phenylacetonitrile as the condensing reagent. MS m/z=442[M+Na]$^+$. Calc'd for C$_{21}$H$_{21}$N$_7$O$_3$: 419.17.

Preparation XXV
7-(Trifluoromethyl)-1,2,3,4-tetrahydroquinoline (440 mg, 2.2 mmol) was dissolved in DMF (10 mL) under N$_2$ at RT. DIEA (284 mg, 2.2 mmol) was added, and the reaction solution was cooled to 0° C. 2,4-Dichloro-1,3,5-triazine was added, and reaction was stirred with gradual warming to RT. The reaction was quenched after 3 h with water, which caused a fine precipitate to form, which is not filterable. This mixture was extracted 3 times with EtOAc. The EtOAc extracts were washed brine, combined, dried over Na$_2$SO$_4$, filtered, concentrated, and dried under high vacuum giving 1-(4-chloro-[1,3,5]triazin-2-yl)-7-trifluoromethyl-1,2,3,4-tetrahydro-quinoline as a yellow oil that was used without further purification.

Preparation XXVI
2,4-Dichloro-1,3,5-triazine (1.95 g, 13 mmol) was dissolved in DMF (50 mL) under N$_2$ and cooled to 0° C. DIEA (1.68 g, 13 mmol) was added, followed by the addition of 6-methyl-1,2,3,4-tetrahydroquinoline (1.91 g, 13 mmol). The reaction was stirred with gradual warming to RT. The reaction was quenched after 3 h with water, which caused a sticky precipitate to form. The mixture was extracted 3 times with EtOAc. The EtOAc extracts were washed brine, combined, dried over Na$_2$SO$_4$, filtered, and concentrated, then dried under high vacuum to remove residual traces of DMF. The recovered material was purified by silica gel chromatography (5%, 10%, 20% and 40% EtOAc/Hexane step gradient) giving 1-(4-chloro-[1,3,5]triazin-2-yl)-6-methyl-1,2,3,4-tetrahydro-quinoline as a white solid.

Preparation XXVII
2,4-Dichloro-1,3,5-triazine (3 g, 20 mmol) was dissolved in DMF (20 mL) under N$_2$ and cooled to 0° C. DIEA (2.58 g, 20 mmol) was added, followed by 3-chloro-6-methylaniline (2.83 g, 20 mmol). The reaction solution was stirred with gradual warming to RT. The reaction was quenched after 3 h with water, then extracted 3 times with EtOAc. The EtOAc extracts were washed with brine, combined, dried over Na$_2$SO$_4$, filtered, and concentrated. The crude was purified by silica gel chromatography (25%, 40%, 60% EtOAc/Hexane step gradient) giving (5-chloro-2-methyl-phenyl)-(4-chloro-[1,3,5]triazin-2-yl)-amine as a white solid.

Preparation XXVIII
The compounds below were prepared according to the procedure for Example 2, Steps 4 and 5, below, substituting the appropriate amines in each of the two reaction steps:
3-{3-[4-(3,4,5-trimethoxy-phenylamino)-[1,3,5]triazin-2-yl]-pyridin-2-ylamino}-benzonitrile;
1-(3-{3-[4-(3,4,5-trimethoxy-phenylamino)-[1,3,5]triazin-2-yl]-pyridin-2-ylamino}-phenyl)-ethanone;
{4-[2-(4-chloro-2-methyl-phenylamino)-pyridin-3-yl]-[1,3,5]triazin-2-yl}-(3,4,5-trimethoxy-phenyl)-amine;
(3,4,5-trimethoxy-phenyl)-[4-(2-vinylamino-pyridin-3-yl)-[1,3,5]triazin-2-yl]-amine;
N1-{3-[4-(3,4,5-trimethoxy-phenylamino)-[1,3,5]triazin-2-yl]-pyridin-2-yl}-propane-1,3-diamine;
3-{3-[4-(3,4,5-Trimethoxy-phenylamino)-[1,3,5]triazin-2-yl]-pyridin-2-ylamino}-benzamide; and
[4-(2-amino-pyridin-3-yl)-[1,3,5]triazin-2-yl]-(3,4,5-trimethoxy-phenyl)-amine.

Preparation XXIX
Oxindole (176 mg, 1.32 mmol) was dissolved in a 1:1 mixture of THF:DMF (4 mL), under N$_2$, at RT. NaH (53 mg of a 60% suspension in mineral oil, 1.32 mmol) was added, which produced a vigorous gas evolution. This mixture was stirred for 30 min at RT, then (4-chloro-[1,3,5]triazin-2-yl)-(3,4,5-trimethoxy-phenyl)amine (156 mg, 0.53 mmol) was added and the reaction was heated to 80° C. for 2 h. The reaction was cooled to RT, partially concentrated under reduced pressure, diluted with EtOAc, then extracted with water. The water extract was back extracted two times with fresh EtOAc. All of the EtOAc extracts were washed with brine, combined, dried over NaSO$_4$, filtered and concentrated. The recovered material was purified by preparative HPLC (5 to 100% CH$_3$CN:H$_2$O (0.1% TFA buffer) over 10 min at 20 mL/min) Crystals formed in the recovered eluant, which were recovered by vacuum filtration, washed with water, and dried under high vacuum giving 3-[4-(3,4,5-trimethoxy-phenylamino)-[1,3,5]triazin-2-yl]-1H-indol-2-ol as a yellow solid: MS m/z=394 [M+H]$^+$. Calc'd for C$_{20}$H$_{19}$N$_5$O$_4$: 393.14.

Similarly, 1-methyl-3-[4-(3,4,5-trimethoxy-phenylamino)-[1,3,5]triazin-2-yl]-1H-indol-2-ol was prepared from (4-chloro-[1,3,5]triazin-2-yl)-(3,4,5-trimethoxy-phenyl)amine (130 mg, 0.44 mmol) was reacted with N-methylindolin-2-one (162 mg, 1.1 mmol, prepared according to the procedure of Bordwell and Fried, *J. Org. Chem.*, (1991) 56, 4218–4223, as a yellow solid: MS m/z= 408 [M+H]$^+$. Calc'd for C$_{21}$H$_{21}$N$_5$O$_4$: 407.16.

Similarly 5-chloro-3-[4-(3,4,5-trimethoxy-phenylamino)-[1,3,5]triazin-2-yl]-1H-indol-2-ol was prepared from (4-chloro-[1,3,5]triazin-2-yl)-(3,4,5-trimethoxy-phenyl) amine (134 mg, 0.45 mmol) and 5-chloro-oxindole (189 mg, 1.1 mmol) giving a yellow solid: MS m/z=428 [M+H]$^+$. Calc'd for C$_{20}$H$_{18}$ClN$_5$O$_4$: 427.10.

Preparation XXX

A mixture of [4-(2-chloro-benzimidazol-1-yl)-[1,3,5] triazin-2-yl]-(3,4,5-trimethoxy-phenyl)amine (Example 1, step 1)(41 mg, 0.10 mmol), 3-aminobenzamide (14 mg, 0.10 mmol) and DIEA (16 mg, 0.12 mmol) in IpOH (3.5 mL) was heated at 100–130° C. for 10–40 h. On cooling a precipitate formed which was collected, washed with IpOH, ether and dried to give 3-{1-[4-(3,4,5-trimethoxy-phenylamino)-[1,3, 5]triazin-2-yl]-1H-benzoimidazol-2-ylamino}-benzamide as a yellow solid.

Compounds below were synthesized according to the procedure outlined above, substituting the appropriate reagents:

4-{1-[4-(3,4,5-trimethoxy-phenylamino)-[1,3,5]triazin-2-yl]-1H-benzoimidazol-2-ylamino}-benzonitrile;
2-{1-[4-(3,4,5-trimethoxy-phenylamino)-[1,3,5]triazin-2-yl]-1H-benzoimidazol-2-ylamino}-benzamide;
3-{1-[4-(3,4,5-trimethoxy-phenylamino)-[1,3,5]triazin-2-yl]-1H-benzoimidazol-2-ylamino}-benzoic acid methyl ester;
3-{1-[4-(3,4,5-trimethoxy-phenylamino)-[1,3,5]triazin-2-yl]-1H-benzoimidazol-2-ylamino}-benzoic acid;
(1H-indazol-6-yl)-{1-[4-(3,4,5-trimethoxy-phenylamino)-[1,3,5]triazin-2-yl]-1H-benzoimidazol-2-yl}-amine;
(1H-indazol-5-yl)-{1-[4-(3,4,5-trimethoxy-phenylamino)-[1,3,5]triazin-2-yl]-1H-benzoimidazol-2-yl}-amine;
(3-nitrobenzyl)-{1-[4-(3,4,5-trimethoxy-phenylamino)-[1,3,5]triazin-2-yl]-1H-benzoimidazol-2-yl}-amine;
(4-bromobenzyl)-{1-[4-(3,4,5-trimethoxy-phenylamino)-[1,3,5]triazin-2-yl]-1H-benzoimidazol-2-yl}-amine;
(3-bromobenzyl)-{1-[4-(3,4,5-trimethoxy-phenylamino)-[1,3,5]triazin-2-yl]-1H-benzoimidazol-2-yl}-amine; and
(4-nitrobenzyl)-{1-[4-(3,4,5-trimethoxy-phenylamino)-[1,3,5]triazin-2-yl]-1H-benzoimidazol-2-yl}-amine.

Preparation XXXI

The compounds below were prepared according to the procedure for Example 1, Step 1, below, substituting the appropriate benzimidazole:

[4-(2-chloro-5-methoxy-benzoimidazol-1-yl)-[1,3,5]triazin-2-yl]-(3,4,5-trimethoxy-phenyl)-amine; and
[4-(2-chloro-6-methoxy-benzoimidazol-1-yl)-[1,3,5]triazin-2-yl]-(3,4,5-trimethoxy-phenyl)-amine.

Preparation XXXII 2,4-Dichloro-1,3,5-triazine (89.1 mg, 0.5944 mmol) was dissolved in DMF (0.5 ml) and cooled to 0° C. To this solution were added DIEA (104 µl), 4-methoxy-3-(2-methoxy-ethoxy)phenylamine (TFA salt)(264 mg, ~0.59 mmol) and DIEA (208 µl) in DMF (1 ml). The reaction mixture was kept at 0° C. for 15 to 30 min and then at RT for 15 min to 2 h. The reaction mixture was diluted with EtOAc and washed with brine. The organic layer was dried over Na$_2$SO$_4$, filtered, and evaporated in vacuo, to give (4-chloro-[1,3,5]triazin-2-yl)-[4-methoxy-3-(2-methoxy-ethoxy)-phenyl]amine.

Preparation XXXIII 1143 (43 mg, 0.2862 mmol) was dissolved in 0.5 ml DMF and cooled to 0° C. DIEA (0.05 ml) was added to the solution. After 5 min this solution was added dropwise to a solution of 3-aminophenylacetamide (43 mg=0.2862 mmol) in 0.5 ml DMF at 0° C. The solution was stirred at 0° C. for 15 min and then at RT for 1 h. To the crude intermediate was added additional DIEA (0.050 ml) and 2-aminobenzimidazole (38 mg, 0.2862 mmol). The mix was heated at 100–120° C. for 18 h. The reaction was cooled to RT and diluted with EtOAc. The organic phase was washed with H$_2$O and brine, dried over Na$_2$SO$_4$, and concentrated down under reduced pressure. The crude was eluted on 2×1.0 mm silica gel prep plates with 5% MeOH/CH$_2$Cl$_2$. The major band was extracted with 15% MeOH/CH$_2$Cl$_2$, yielding. 2-{3-[4-(2-amino-benzoimidazol-1-yl)-[1,3,5] triazin-2-ylamino]-phenyl}-acetamide. MS m/z=361 [M+H] Calc'd for C$_{18}$H$_{16}$N$_8$O: 360.14.

The following compounds are prepared according to the above procedure.

2-{3-[4-(2-Amino-benzoimidazol-1-yl)-[1,3,5]triazin-2-ylamino]-phenyl}-N-pyridin-2-ylmethyl-acetamine. MS m/z=452 [M+H] Calc'd for C$_{24}$H$_{21}$N$_9$O: 451.19.
1-[4-(3-[1,2,3]Triazol-1-ylmethyl-phenylamino)-[1,3,5] triazin-2-yl]-1H-benzoimidazol-2-ylamine. MS m/z=385 MS m/z=385 [M+H] Calc'd for C$_{19}$H$_{16}$N$_{10}$: 384.16.

EXAMPLE 1

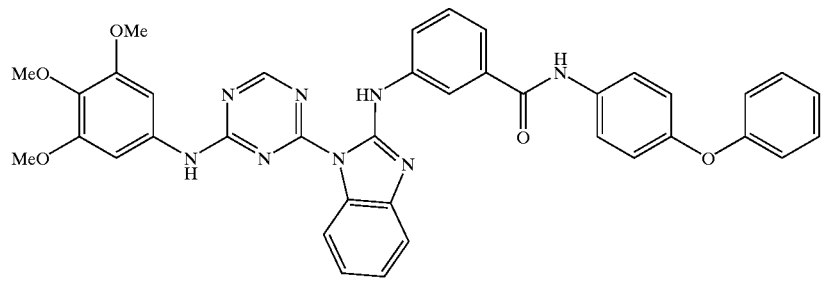

N-(4-Phenoxyphenyl)-3-{1-[4-(3,4,5-trimethoxy-phenylamino)-[1,3,5]triazin-2-yl]-1H-benzimidazo-1-2-ylamino}benzamide Step 1. Preparation of [4-(2-chloro-benzimidazol-1-yl)-[1,3,5]triazin-2-yl]-(3,4,5-trimethoxy-phenyl)amine To a suspension of (4-chloro-[1,3,5]triazin-2-yl)-(3,4,5-trimethoxy-phenyl)amine (2.97 g, 10 mmol) and 2-chlorobenzimidazole (1.53 g, 10 mmol) in dry AcCN (100 mL) was added ground $K_2CO_3$ (1.68 g, 12 mmol). The resulting mixture was heated at 65° C. for 4 h, cooled to RT, concentrated in vacuo and purified by column chromatography (EtOAc/n-Hexanes) to provide [4-(2-chloro-benzimidazol-1-yl)-[1,3,5]triazin-2-yl]-(3,4,5-trimethoxy-phenyl)amine as a white powder. MS m/z 413=[M+H]$^+$. Calc'd for $C_{19}H_{17}ClN_6O_3$: 412.11:

Step 2. Preparation of N-(4-phenoxyphenyl)-3-{1-[4-(3,4,5-trimethoxy-phenylamino)-[1,3,5]triazin-2-yl]-1H-benzimidazo-1-2-ylamino}benzamide To 96 mg (0.23 mmol) of [4-(2-chloro-benzimidazol-1-yl)-[1,3,5]triazin-2-yl]-(3,4,5-trimethoxy-phenyl)-amine (Step 1) were added 3-amino-N-(4-phenoxyphenyl)benzamide (74.3 mg, 0.24 mmol), DIEA (0.061 ml), and IpOH (2 ml). The mixture was heated overnight in a sealed tube at 100° C. The reaction mixture was cooled to RT, diluted with $CH_2Cl_2$, and washed with 2N HCl, water, and then brine. The organic layer was dried over $Na_2SO_4$ and filtered. Upon sitting at RT for several hours, a white solid precipitated out of $CH_2Cl_2$. The solid was filtered and dried, yielding the product. MS m/z 681=[M+H]$^+$. Calc'd for $C_{38}H_{32}N_8O5$: 680.722.

EXAMPLE 2A

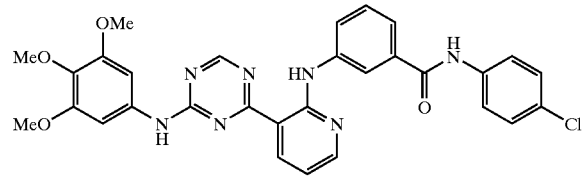

N-(4-Chlorophenyl)-3-{3-[4-(3,4,5-trimethoxy-phenylamino)-[1,3,5]triazin-2-yl]-pyridin-2-ylamino}-benzamide

EXAMPLE 2B

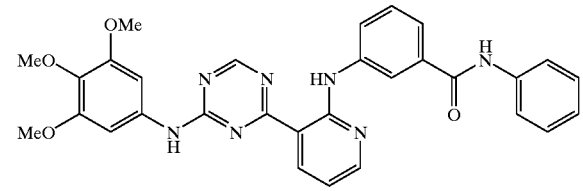

N-(Phenyl)-3-{3-[4-(3,4,5-trimethoxy-phenylamino)-[1,3,5]triazin-2-yl]-pyridin-2-ylamino}benzmide Step 1: Preparation of 2-chloro-nicotinamidine 2-Chloro-3-cyanopyridine (5.0 g, 36 mmol) was dissolved in dry EtOH (100 mL) at 0° C. HCl was bubbled through the mixture for 3 h and the mixture was sealed and refrigerated (about 8° C.) overnight. After concentration, the residue was stirred with ammonium acetate (5.5 g) in 100 mL IpOH. After 12 h, the pH was adjusted to 9 (from 4) using concentrated $NH_4OH$ solution, and stirring continued two more days. The mixture was concentrated and purified by flash chromatography (10:1:0.1 $CH_2Cl_2$/MeOH/$NH_4OH$). Trituration in hot tBuOMe/IpOH removed some residual amide side-product to provide the amidine, 2-chloro-nicotinamidine as a white solid.

Step 2: Preparation of amino-(2-chloro-pyridin-3-yl)-methylcyanamide

2-Chloro-nicotinamidine (Step 1) was suspended in 10 mL IpOH with 500 mg solid cyanamide and the stirring solids were dissolved by addition of 5% aqueous $NaHCO_3$ (30 mL). After two days stirring, the amino-(2-chloro-pyridin-3-yl)-methylcyanamide was isolated by EtOAc extraction of the aqueous reaction mixture followed by flash chromatography using 95:5:0.5 $CH_2Cl_2$/MeOH/$NH_4OH$. MS m/z=181 [M+H]$^+$. Calc'd for $C_7H_6N_4Cl$:181.03.

Step 3: Preparation of 2-chloro-4-(2-chloro-pyridin-3-yl)-[1,3,5]triazine

Amino-(2-chloro-pyridin-3-yl)-methylcyanamide (Step 2) (3.5 g) was added as a solid to a stirring, 0° C. solution of $POCl_3$ (2.3 ml, 25 mmol) and DMF (1.9 ml, 25 mmol) in 100 ml AcCN. The clear solution was stirred at RT for 1 h, concentrated, and immediately filtered through a plug of silica. Concentration provided 2-chloro-4-(2-chloro-pyridin-3-yl)-[1,3,5]triazine as a white solid. MS m/z=227 [M+H]$^+$. Calc'd for $C_8H_4Cl_2N_4$: 225.98.

Step 4: Preparation of [4-(2-chloro-pyridin-3-yl)-[1,3,5]triazin-2-yl]-(3,4,5-trimethoxy-phenyl)amine 2-Chloro-4-(2-chloro-pyridin-3-yl)-[1,3,5]triazine (1.7 g, 7.5 mmol) was stirred overnight at RT with 3,4,5-trimethoxyaniline (1.5 g, 8.3 mmol) in IpOH (200 mL). After addition of $Et_3N$ (2 ml), stirring was continued for an additional day. The mixture was concentrated, triturated with t-BuOMe and filtered, rinsing with a small amount of IpOH. The [4-(2-chloro-pyridin-3-yl)-[1,3,5]triazin-2-yl]-(3,4,5-trimethoxy-phenyl)amine (2.5 g) was isolated as the $Et_3HN^+Cl^-$ salt. Part of this material was filtered through a plug of silica and analyzed. MS m/z=374 [M+H]$^+$; 3H). Calc'd for $C_{17}H_{16}ClN_5O_3$: 373.09. Remaining material was used without filtering in the next step.

Step 5: Preparation of N-(phenyl)-3-{3-[4-(3,4,5-trimethoxy-phenylamino)-[1,3,5]triazin-2-yl]-pyridin-2-ylamino}benzamide and N-(4-chloro-phenyl)-3-{3-[4-(3,4,5-trimethoxy-phenylamino)-[1,3,5]triazin-2-yl]-pyridin-2-ylamino}benzamide To [4-(2-chloro-pyridin-3-yl)-[1,3,5]triazin-2-yl]-(3,4,5-trimethoxy-phenyl)-amine (Step 4) (94 mg, 0.25 mmol) was added 3-amino-N-(4-chlorophenyl)benzamide (185 mg, 0.74 mmol) in 150 ml DMSO, and the mixture was stirred overnight at 90–95° C. The resulting crude mixture contained an impurity originating from a side product in the aniline starting material. The material was purified by silica gel chromatography [1:1:1 hexanes/$CH_2Cl_2$/t-BuOMe with ramping 10:1 MeOH/$NH_4OH$], and then triturated in a EtOAc/MeOH mixture and filtered to obtain a yellow solid, a 10:1 mixture of the two compounds:

N-(4-Chloro-phenyl)-3-{3-[4-(3,4,5-trimethoxy-phenylamino)-[1,3,5]triazin-2-yl]-pyridin-2-ylamino}benzamide: MS m/z 584.5=[M+H]$^+$. Calc'd for $C_{30}H_{26}ClN_7O_4$: 583.17.

N-phenyl-3-{4-(3,4,5-trimethoxy-phenylamino)-[1,3,5]triazin-2-yl]-pyridin-2-ylamino}benzamide: MS m/z 550.3=[M+H]$^+$. Calc'd for $C_{30}H_{27}N_7O_4$: 549.21.

EXAMPLE 3

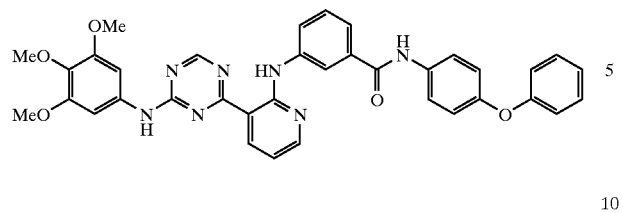

N-(4-Phenoxy-phenyl)-3-{3-[4-(3,4,5-trimethoxy-phenylamino)-[1,3,5]triazin-2-yl]-pyridin-2-ylamino}-benzamide To [4-(2-chloro-pyridin-3-yl)-[1,3,5]triazin-2-yl]-(3,4,5-trimethoxy-phenyl)amine (Example 2, Step 4)(103 mg, 0.275 mmol) was added 3-amino-N-(4-phenoxyphenyl)-benzamide (297 mg, 0.975 mmol) and DMSO (150 ml), and the mixture was heated overnight at 90° C. The residue was treated with IpOH and MeOH, triturated, sonicated, and filtered to obtain N-(4-phenoxy-phenyl)-3-{3-[4-(3,4,5-trimethoxy-phenylamino)-[1,3,5]triazin-2-yl]-pyridin-2-ylamino}benzamide as a yellow solid: MS m/z 642.5=[M+H]$^+$. Calc'd for $C_{36}H_{31}N_7O_5$: 641.24.

EXAMPLE 4

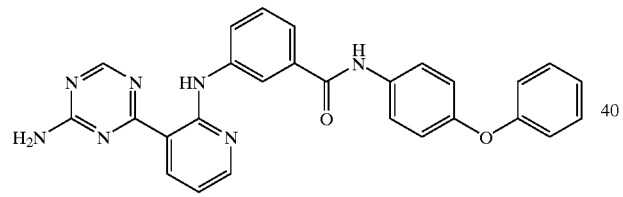

3-[3-(4-Amino-[1,3,5]triazin-2-yl)-pyridin-2-ylamino]-N-(4-phenoxy-phenyl)benzamide

[4-(2-Chloro-pyridin-3-yl)-[1,3,5]triazin-2-yl]-(3,4,5-trimethoxy-phenyl)amine (Example 2, Step 4) (247 mg, 1.08 mmol) was suspended in a 2 M solution of $NH_3$ in IpOH (3 ml)(Aldrich), and the reaction mixture was stirred overnight in a sealed tube. Concentration, trituration in a small amount of MeOH, and filtration provided a white solid. A portion of this material (97 mg, 0.47 mmol) was mixed with 3-amino-N-(4-phenoxyphenyl)benzamide (320 mg, 0.96 mmol) and DMSO (250 ml), and stirred overnight at 90° C. The dark residue was diluted with IpOH, sonicated, triturated, and then concentrated. Upon dilution with IpOH, a light green solid was isolated by filtration. MS m/z=476.5. [M+H]$^+$. Calc'd for $C_{27}H_{21}N_7O_2$: 475.18.

EXAMPLE 5

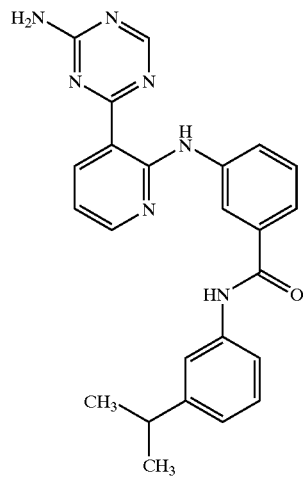

3-[3-(4-Amino-[1,3,5]triazin-2-yl)-pyridin-2-ylamino]-N-(3-isopropyl-phenyl)-benzamide 3-[3-(4-Amino-[1,3,5]triazin-2-yl)-pyridin-2-ylamino]-N-(3-isopropyl-phenyl)-benzamide was prepared in the same manner as Example 4. MS m/z=426.2 [M+H]. Calc'd for $C_{24}H_{23}N_7O$: 425.20.

Other compounds included in this invention are set forth in Tables 1–2 below.

TABLE 1

| # | R$^2$ | R$^{1a}$ |
|---|---|---|
| 6. | amino- | 4-chlorophenyl |
| 7. | amino- | 3-isoquinolinyl |
| 8. | amino- | 2-quinolinyl |
| 9. | amino- | 2-benzthiazolyl |
| 10. | amino- | 2-benzimidazolyl |
| 12. | amino- | 4-benzimidazolyl |
| 13. | amino- | 5-benzimidazolyl |
| 14. | amino- | 6-benzimidazolyl |
| 15. | amino- | 7-benzimidazolyl |
| 16. | amino- | 2-chlorophenyl |
| 17. | Br | 3-isoquinolinyl |
| 18. | Br | 2-quinolinyl |
| 19. | Br | 2-benzthiazolyl |
| 20. | Br | 2-benzimidazolyl |
| 21. | Cl | 4-benzimidazolyl |
| 22. | Cl | 5-benzimidazolyl |
| 23. | Cl | 6-benzimidazolyl |
| 24. | Cl | 7-benzimidazolyl |
| 25. | Cl | 4-chlorophenyl |
| 26. | hydroxy- | 4-chlorophenyl |
| 27. | amino- | 4-chlorophenyl |

TABLE 1-continued

| # | R$^{1A}$ | R$^2$ |
|---|---|---|
| 28. | 4-phenoxyphenyl | amino |
| 29. | 3-phenoxyphenyl | methoxy |
| 30. | 4-biphenyl | methoxy |
| 31. | 4-cyclohexylphenyl | methoxy |
| 32. | 2-quinolyl | methoxy |
| 33. | 3-isoquinolyl | methoxy |
| 34. | 3-quinolyl | methoxy |
| 35. | 1-isoquinolyl | methoxy |
| 36. | 5-quinolyl | methoxy |
| 37. | 5-isoquinolyl | methoxy |
| 38. | 6-quinolyl | methoxy |
| 39. | 6-isoquinolyl | methoxy |
| 40. | 7-quinolyl | methoxy |
| 41. | 7-isoquinolyl | hydroxy |
| 42. | 4-quinolyl | hydroxy |
| 43. | 4-isoquinolyl | hydroxy |
| 44. | 4-pyridyl | hydroxy |
| 45. | 4-pyrimidinyl | hydroxy |
| 46. | 2-pyrimidinyl | hydroxy |
| 47. | 6-pyrimidinyl | hydroxy |
| 48. | 4-pyridazinyl | hydroxy |
| 49. | 5-pyridazinyl | hydroxy |

| # | R$^{1a}$ | R$^2$ |
|---|---|---|
| 50. | 4-indolyl | hydroxy |
| 51. | 5-isoindolyl | CH$_3$ |
| 52. | 5-naphthyridinyl | CH$_3$ |
| 53. | 6-quinozalinyl | 3-amino |
| 54. | 6-isoquinolyl | CH$_3$ |
| 55. | 4-naphthyridinyl | CH$_3$ |
| 56. | 5-quinozalinyl | CH$_3$O |
| 57. | 4-naphthyridinyl | CH$_3$ |
| 58. | 3,4-dichlorophenyl | CH$_3$ |
| 59. | 6-isoquinolyl | CH$_3$ |
| 60. | 4-chlorophenyl | CH$_3$ |
| 61. | 4-chlorophenyl | CH$_3$ |
| 62. | 6-indazolyl | hydroxymethyl |
| 63. | 6-isoindolyl | hydroxymethyl |
| 64. | 5-indazolyl | hydroxymethyl |
| 65. | 5-isoindolyl | hydroxymethyl |
| 66. | 6-benzothienyl | hydroxymethyl |
| 67. | 6-benzofuryl | hydroxymethyl |
| 68. | 5-benzothienyl | hydroxymethyl |
| 69. | 5-benzofuryl | hydroxymethyl |
| 70. | 2-benzimidazolyl | hydroxymethyl |
| 71. | 2-benzoxazolyl | hydroxymethyl |

| # | R$^{1A}$ | R$^2$ |
|---|---|---|
| 72. | 6-benzimidazolyl | hydroxymethyl |
| 73. | 6-benzoxazolyl | hydroxymethyl |
| 74. | 6-benzthiazolyl | Cl |
| 75. | 2-quinazolinyl | hydroxymethyl |
| 76. | 4-tertbutylphenyl | Cl |
| 77. | 4-cyclohexyloxyphenyl | Cl |
| 78. | 4-(3-thienyl)phenyl | Br |
| 79. | 4-(pyrazol-3-yl)phenyl | amino |
| 80. | 4-pyridyl | Cl |
| 81. | 3-methoxyphenyl | Cl |
| 82. | 4-sec-butylphenyl | Cl |
| 83. | 4-isopropylphenyl | Br |

TABLE 2

| # | R$^2$ | R$^{1a}$ |
|---|---|---|
| 84. | 4-amino- | 4-chlorophenyl |
| 85. | 4-amino- | 3-isoquinolinyl |
| 86. | 4-amino- | 2-quinolinyl |
| 87. | 4-amino- | 2-benzthiazolyl |
| 88. | 4-amino- | 2-benzimidazolyl |
| 89. | 4-amino- | 4-benzimidazolyl |
| 90. | 4-amino- | 5-benzimidazolyl |
| 91. | 4-amino- | 6-benzimidazolyl |
| 92. | 4-amino- | 7-benzimidazolyl |
| 93. | Br | 2-chlorophenyl |
| 94. | Br | 3-isoquinolinyl |
| 95. | Br | 2-quinolinyl |
| 96. | Br | 2-benzthiazolyl |
| 97. | Br | 2-benzimidazolyl |
| 98. | Br | 4-benzimidazolyl |
| 99. | Br | 5-benzimidazolyl |
| 100. | Br | 6-benzimidazolyl |
| 101. | Br | 7-benzimidazolyl |
| 102. | Br | 4-chlorophenyl |
| 103. | hydroxy | 4-chlorophenyl |
| 104. | phenyl | 4-chlorophenyl |

| # | R$^{1a}$ | R$^2$ |
|---|---|---|
| 105. | 4-phenoxyphenyl | H |
| 106. | 3-phenoxyphenyl | methoxy |
| 107. | biphenyl | methoxy |
| 108. | 4-cyclohexylphenyl | methoxy |
| 109. | 2-quinolyl | methoxy |
| 110. | 6-benzothienyl | hydroxymethyl |
| 111. | 6-benzofuryl | hydroxymethyl |
| 112. | 4-tertbutylphenyl | Cl |
| 113. | 4-propylphenyl | Br |
| 114. | 4-isopropylphenyl | Cl |
| 115. | 4-isobutylphenyl | phenyl |
| 116. | 4-sec-butylphenyl | amino |

Although the pharmacological properties of the compounds of Formula I vary with structural change, in general, activity possessed by compounds of Formula I may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed inhibition of KDR kinase at doses less than 50 µm.

BIOLOGICAL EVALUATION

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS + antibiotics, and spun at 1000 rpm for 10 min. Prior to centrifugation of the cells, a small amount is collected for a cell count. After centrifugation, the medium is discarded, and the cells are resuspended in the appropriate volume of DMEM+10% FBS + antibiotics to achieve a concentration of $3 \times 10^5$ cells/mL. Another cell count is performed to confirm the cell concentration. The cells are diluted to $3 \times 10^4$ cells/mL in DMEM+10% FBS + antibiotics, and 100 µL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 µL of each compound dilution are diluted further in a total of 1 mL DMEM+10% FBS + antibiotics (400× dilution). Medium containing 0.25% DMSO is also prepared for the 0 µM compound sample. At the 22-hour timepoint, the medium is removed from the cells, and 100 µL of each compound dilution is added. The cells are incubated at 37° C. for 2–3 h.

During the compound pre-incubation period, the growth factors are diluted to the appropriate concentrations. Solutions of DMEM+10% FBS + antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 µL of each will be added to the cells (110 µL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50–0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. $IC_{50}$ values are then determined.

Angiogenesis Model

To determine the effects of the present compounds on angiogenesis in vivo, selective compounds are tested in the rat corneal neovascularization micropocket model or the angiogenesis assay of Passaniti, Lab. Invest., 67, 519–28 (1992).

Rat Corneal Neovascularization Micropocket Model

In Life Aspects: Female Sprague Dawley rats weighing approximately 250 g were randomized into one of five treatment groups. Pretreatment with the vehicle or compound was administered orally, 24 h prior to surgery and continued once a day for seven additional days. On the day of surgery, the rats were temporarily anesthetized in an Isofluorane gas chamber (delivering 2.5 liters/min oxygen+ 5% Isofluorane). An othoscope was then placed inside the mouth of the animal to visualize the vocal cords. A tip-blunted wire was advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) was connected to the endotracheal tube to deliver a mixture of oxygen and 3% Isofluorane. Upon achieving deep anesthesia, the whiskers were cut short and the eye areas and eyes gently washed with Betadine soap and rinsed with sterile saline. The corneas were irrigated with one to two drops of Proparacaine HCl ophthalmic topical anesthetic solution (0.5%)(Bausch and Lomb Pharmaceuticals, Tampa Fla.). The rat was then positioned under the dissecting microscope and the corneal surface brought into focus. A vertical incision was made on the midline of the cornea using a diamond blade knife. A pocket was created by using fine scissors to separate the connective tissue layers of the stroma, tunneling towards the limbus of the eye. The distance between the apex of the pocket and the limbus was approximately 1.5 mm. After the pocket had been made, the soaked nitrocellulose disk filter (Gelman Sciences, Ann Arbor Mich.) was inserted under the lip of the pocket. This surgical procedure was performed on both eyes. rHu-bFGF soaked disks were placed into the right eye, and the rHu-VEGF soaked disks were placed into the left eye. Vehicle soaked disks were placed in both eyes. The disk was pushed into position at the desired distance from the limbal vessels. Ophthalmic antibiotic ointment was applied to the eye to prevent drying and infection. After seven days, the rats were euthanized by $CO_2$ asphyxiation, and the eyes enucleated. The retinal hemisphere of the eye was windowed to facilitate fixation, and the eye placed into formalin overnight.

Post Mortem Aspects: After twenty-four hours in fixative, the corneal region of interest was dissected out from the eye, using fine forceps and a razorblade. The retinal hemisphere was trimmed off and the lens extracted and discarded. The corneal dome was bisected and the superfluous cornea trimmed off. The iris, conjunctiva and associated limbal glands were then carefully teased away. Final cuts were made to generate a square 3×3 mm containing the disk, the limbus, and the entire zone of neovascularization.

Gross Image Recording: The corneal specimens were digitally photographed using a Sony CatsEye DKC5000 camera (A. G. Heinz, Irvine Calif.) mounted on a Nikon SMZ-U stereo microscope (A. G. Heinz). The corneas were submerged in distilled water and photographed via trans-illumination at approximately 5.0 diameters magnification.

Image Analysis: Numerical endpoints were generated using digital micrographs collected from the whole mount corneas after trimming and were used for image analysis on the Metamorph image analysis system (Universal Imaging Corporation, West Chester Pa.). Three measurements were taken: Disk placement distance from the limbus, number of vessels intersecting a 2.0 mm perpendicular line at the midpoint of the disk placement distance, and percent blood vessel area of the diffusion determined by thresholding.

General Formulations:

0.1% BSA in PBS Vehicle: 0.025 g of BSA was added to 25.0 ml of sterile 1× phosphate buffered saline, gently shaken until fully dissolved, and filtered at 0.2 μm. Individual 1.0 ml samples were aliquoted into 25 single use vials, and stored at −20° C. until use. For the rHu-bFGF disks, a vial of this 0.1% BSA solution was allowed to thaw at room temperature. Once thawed, 10 μl of a 100 mM stock solution of DTT was added to the 1 ml BSA vial to yield a final concentration of 1 mM DTT in 0.1% BSA.

rHu-VEGF Dilutions:

Prior to the disk implant surgery, 23.8 μl of the 0.1% BSA vehicle above was added to a 10 μg rHu-VEGF lyophilized vial yielding a final concentration of 10 μM.

rHu-bFGF: Stock concentration of 180 ng/μl:

R&D rHu-bFGF: Added 139 μl of the appropriate vehicle above to the 25 μg vial lyophilized vial. 13.3 μl of the [180 ng/μl] stock vial and added 26.6 μl of vehicle to yield a final concentration of 3.75 μM concentration.

Nitro-cellulose Disk Preparation: The tip of a 20-gauge needle was cut off square and beveled with emery paper to create a punch. This tip was then used to cut out ≈0.5 mm diameter disks from a nitrocellulose filter paper sheet (Gelman Sciences). Prepared disks were then placed into Eppendorf microfuge tubes containing solutions of either 0.1% BSA in PBS vehicle, 10 μM rHu-VEGF (R&D Systems, Minneapolis, Minn.), or 3.75 μM rHu-bFGF (R&D Systems, Minneapolis, Minn.) and allowed to soak for 45–60 min before use. Each nitrocellulose filter disk absorbs approximately 0.1 μl of solution.

In the rat micropocket assay, compounds of the present invention will inhibit angiogenesis at a dose of less than 50 mg/kg/day.

Tumor Model

A431 cells (ATCC) are expanded in culture, harvested and injected subcutaneously into 5–8 week old female nude mice (CD1 nu/nu, Charles River Labs) (n=5–15). Subsequent administration of compound by oral gavage (10–200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention are active at doses less than 150 mpk.

Rat Adjuvant Arthritis Model

The rat adjuvant arthritis model (Pearson, Proc. Soc. Exp. Biol. 91, 95–101 (1956)) is used to test the anti-arthritic activity of compounds of the formula 1, or salts thereof. Adjuvant Arthritis can be treated using two different dosing schedules: either (i) starting time of immunization with adjuvant (prophylactic dosing); or from day 15 when the arthritic response is already established (therapeutic dosing). Preferably a therapeutic dosing schedule is used.

Rat Carrageenan-induced Analgesia Test

The rat carrageenan analgesia test was performed with materials, reagents and procedures essentially as described by Hargreaves, et al., (Pain, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined.

Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anti-cancer agent, an anti-viral agent, antiinflammatory agent, antifungal agent, antibiotic, or an anti-vascular hyperproliferation compound; and any pharmaceutically acceptable carrier, adjuvant or vehicle. Alternate compositions of this invention comprise a compound of the formulas described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but were not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which were commonly used include lactose and corn starch. Lubricating agents, such as magnesium stearate, were also typically added. For oral administration in a capsule form, useful diluents include lactose and dried corn starch. When aqueous suspensions and/or emulsions were administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may comprise formulations utilizing liposome or microencapsulation techniques. Such techniques were known in the art.

The pharmaceutical compositions of this invention may be administered by nasal aerosol or inhalation. Such compositions were prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Formulations

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units were tablets or capsules. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The amount of compounds which were administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed.

Thus, the dosage regimen may vary widely, but can be determined routinely using standard methods. A daily dose of about 0.01 to 500 mg/kg body weight, preferably between about 0.5 and about 50 mg/kg body weight and most preferably between about 0.1 to 20 mg/kg body weight, may be appropriate may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients were dissolved or suspended in suitable carrier, especially an aqueous solvent for the active ingredients. The active ingredients were preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:

1. A compound of the Formula I

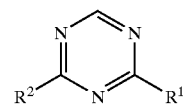

wherein $R^1$ is selected from
   phenyl ortho substituted with $R^{4a}$, and
   heteroaryl selected from isoquinolyl, quinolyl, pyridyl, pyrimidinyl, pyridazinyl, indolyl, isoindolyl, naphthyridinyl, quinozalinyl, tetrahydroquinolinyl, benzothienyl, benzofuryl, benzimidazolyl, benzoxazolyl, and benzthiazolyl, wherein heteroaryl is ortho-substituted with $R^{4a}$;

wherein $R^2$ is selected from fluoro, chloro, bromo, —$NHR^5$, and methyl optionally substituted with phenyl, $R^8$, chloro, fluoro, $OR^5$, $OC(O)R^5$, $NR^5R^5$ and $COOR^5$;

wherein $R^4$ is independently selected from
   $C_1$–$C_4$ alkyl,
   optionally substituted phenyl,
   chloro,
   fluoro,
   $OR^5$, and
   $C_1$–$C_4$ alkyl substituted with 1–3 substituents independently selected from optionally substituted phenyl and $R^8$;

wherein $R^{4a}$ is —$NHR^{16}$;

wherein $R^5$ is independently selected from
   H,
   $C_1$–$C_4$ alkyl,
   $C_3$–$C_4$ cycloalkyl,
   optionally substituted phenyl,
   $R^9$, and
   $C_1$–$C_3$ alkyl substituted with 1–3 substituents independently selected from optionally substituted phenyl, $R^7$ and $R^9$ groups, and wherein $R^{5a}$ is selected from optionally substituted phenyl and $R^{9a}$;

wherein $R^6$ is $C(O)R^5$;

wherein $R^7$ is independently selected from chloro, fluoro, $CF_3$, $OR^{10}$, $NR^{10}R^{10}$, $COOR^{10}$, $NO_2$, CN, and $C(O)R^{10}$;

wherein $R^8$ is 5–6 membered heteroaryl optionally substituted with a substituent independently selected from $C_1$–$C_4$ alkyl, halo, $C_1$–$C_4$ haloalkyl, optionally substituted phenyl, $R^9$, $OR^{10}$, $NR^{10}R^{10}$, $COOR^{10}$, $C(O)R^{10}$, $OC(O)R^{10}$, and $C(O)NR^{10}R^{10}$;

wherein $R^{8a}$ is independently a 5–6 membered heteroaryl, or 9–10 membered heteroaryl comprising 1–2 heteroatoms if monocyclic, or 1–4 heteroatoms if bicyclic, said heteroatoms independently selected from O, N, or S, and wherein 0, 1, or 2 atoms of each ring may be substituted by substituents independently selected from $C_1$–$C_4$ alkyl, optionally substituted phenyl, $R^9$, chloro, fluoro, oxo, $OR^5$, and $C_1$–$C_4$ alkyl substituted with 1–3 substituents independently selected from $R^7$, $R^9$ and optionally substituted phenyl;

provided $R^{8a}$ is substituted with $C(O)NHR^{5a}$;

wherein $R^9$ is independently a 5–6 membered heteroaryl, or 9–10 membered bicyclic heteroaryl, ring system comprising 1–2 heteroatoms if monocyclic or 1–4 heteroatoms if bicyclic, said heteroatoms independently selected from O, N, or S, and wherein 0, 1, or 2 atoms of each ring may be substituted by a substituent independently selected from $C_1$–$C_4$ alkyl, halo, $C_1$–$C_4$ haloalkyl, optionally substituted phenyl, $R^8$, $OR^{10}$, $NR^{10}R^{10}$, $COOR^{10}$, $C(O)R^{10}$, $OC(O)R^{10}$, and $C(O)NR^{10}R^{10}$;

wherein $R^{9a}$ is independently a 5–6 membered heteroaryl, or 9–10 membered heteroaryl bicyclic ring system comprising 1–2 heteroatoms if monocyclic, or 1–3 heteroatoms if bicyclic, said heteroatoms independently selected from O, N, or S, and wherein 0, 1, or 2 atoms of each ring may be substituted by a substituent independently selected from $C_1$–$C_3$ alkyl, halo, oxo, $C_1$–$C_3$ haloalkyl and $OR^{10}$;

wherein $R^{10}$ is independently selected from H, methyl and $C_1$–$C_3$ alkyl substituted with 1–3 substituents independently selected from fluoro, chloro, hydroxy, methoxy, optionally substituted phenyl and $R^9$, and optionally substituted phenyl; and wherein $R^{16}$ is selected from phenyl and $R^{8a}$; provided phenyl is substituted with $C(O)NHR^{5a}$;

wherein optionally substituted phenyl is unsubstituted or substituted with 1–3 substituents independently selected from $C_1$–$C_3$ alkyl, $R^9$, fluoro, chloro, $C_1$–$C_3$ haloalkyl, $OR^{10}$, $NR^{10}R^{10}$, $COOR^{10}$, $C(O)R^{10}$, $C(O)NR^5R^5$, $OC(O)R^{10}$, and $C_1$–$C_3$ alkyl substituted with 1–2 substituents independently selected from phenyl and $R^9$;

or a pharmaceutically acceptable salt thereof.

2. Compound of claim 1 or a pharmaceutically acceptable salt thereof selected from:

N-(4-phenoxyphenyl)-3-{1-[4-(3,4,5-trimethoxy-phenylamino)-[1,3,5]triazin-2-yl]-1H-benzimidazo-1-2-ylamino}benzamide;

N-(4-chlorophenyl)-3-{3-[4-(3,4,5-trimethoxy-phenylamino)-[1,3,5]triazin-2-yl]-pyridin-2-ylamino}-benzamide;

N-(phenyl)-3-{3-[4-(3,4,5-trimethoxy-phenylamino)-[1,3,5]triazin-2-yl]-pyridin-2-ylamino}benzamide;

N-(4-phenoxy-phenyl)-3-{3-[4-(3,4,5-trimethoxy-phenylamino)-[1,3,5]triazin-2-yl]-pyridin-2-ylamino}-benzamide;

3-[3-(4-amino-[1,3,5]triazin-2-yl)-pyridin-2-ylamino]-N-(4-phenoxy-phenyl)benzamide; and 3-[3-(4-amino-[1,3,5]triazin-2-yl)-pyridin-2-ylamino]-N-(3-isopropyl-phenyl)-benzamide.

3. A compound of claim 1 wherein $R^1$ is

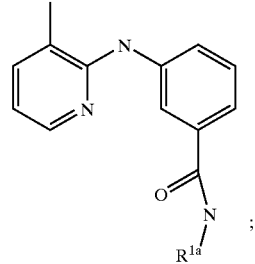

wherein $R^{1a}$ is selected from unsubstituted or substituted aryl, 5–6-membered heteroaryl and 9–10 membered fused heteroaryl, wherein $R^{1a}$ is substituted with one or more substituents independently selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5–6 membered heterocyclyl-$C_1$–$C_2$-alkylenyl, optionally substituted heteroaryl, optionally substituted heteroaryloxy, $C_{1-6}$-haloalkyl, and $C_{1-6}$-alkoxy;

wherein $R^2$ is selected from fluoro, chloro, bromo, $NHR^5$ and methyl optionally substituted with 1 to 3 substituents independently selected from phenyl, $R^9$, chloro, fluoro, $OR^5$, $OC(O)R^5$, $NR^5R^5$ and $COOR^5$;

wherein $R^4$ is selected from $C_1$–$C_4$ alkyl, optionally substituted phenyl, chloro, fluoro, hydroxy, methoxy and benzyl;

wherein $R^5$ is independently selected from H, $C_1$–$C_4$ alkyl, $C_2$–$C_4$ alkenyl, $C_2$–$C_4$ alkynyl, $C_3$–$C_6$ cycloalkyl, $C_4$–$C_6$ cycloalkenyl, $R^9$, phenyl optionally substituted with $R^4$, and $C_1$–$C_4$ alkyl substituted with 1–3 substituents independently selected from aryl, $R^7$ and $R^9$ groups; and wherein $R^9$ is selected from 5–6-membered heteroaryl, and wherein 0, 1, 2 or 3 atoms of each ring may be substituted by a substituent independently selected from $C_1$–$C_4$ alkyl, fluoro, chloro, trifluoromethyl, optionally substituted phenyl, hydroxy, methoxy, amino, methylamino, carboxy, methoxycarbonyl, formyl, methylcarbonyl, acetyl, and aminocarbonyl;

or a pharmaceutically acceptable salt thereof.

4. A compound of claim 3 wherein $R^{1a}$ is selected from phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, and benzthiazolyl;

wherein $R^{1a}$ is substituted with one or more substituents independently selected from chloro, fluoro, amino, hydroxy, cyclohexyl, phenylmethyl, morpholinylmethyl, methylpiperdinylmethyl, methyl, ethyl, propyl, isopropyl, butyl, tert-butyl, sec-butyl, isobutyl, methylpiperazinylmethyl, trifluoromethyl, phenyloxy, methoxy and ethoxy;

wherein $R^2$ is selected from —$NHR^5$, fluoro, chloro, bromo, benzyl, trifluoromethyl, hydroxymethyl, methoxymethyl, aminomethyl and methyl; and wherein $R^5$ is independently selected from H, methyl and phenyl optionally substituted with chloro, fluoro, hydroxy, and methoxy;

or a pharmaceutically acceptable salt thereof.

5. A compound of Formula II

II

[Chemical structure of Formula II showing a triazine linked to a substituted phenyl ring with R$^{5b}$, HN—A$^3$—A$^2$—A$^1$ with ring Z, X$^a$R$^{1a}$, and R$^{4b}$ substituents]

wherein $A^1$, $A^2$ and $A^3$ are independently selected from C, and CH;

wherein ring Z is phenyl; wherein $A^1$ and $A^3$ are C and $A^2$ is CH when Z is phenyl;

wherein $X^a$ together with the $R^{1a}$ group it is bound to is selected from

[Two chemical structures showing acyl groups with Z$^a$, N-R$^{1a}$, R$^5$ substituents]

and wherein $Z^a$ is oxygen or sulfur;

wherein $R^z$ is $C_1$–$C_4$ alkylenyl, where one of the CH$_2$ groups may be substituted with O or an —NH—;

wherein $R^{1a}$ is selected from
 a) substituted or unsubstituted 6–10 membered aryl,
 b) substituted or unsubstituted 5–6 membered heterocyclyl,
 c) substituted or unsubstituted 9–10 membered fused heterocyclyl,
 d) cycloalkyl, and
 e) cycloalkenyl;
  wherein $R^{1a}$ is optionally substituted with one or more substituents independently selected from halo, —OR$^{15}$, —SR$^{15}$, —CO$_2$R$^{15}$, —CONR$^{15}$R$^{15}$, —COR$^{15}$, —NR$^{15}$R$^{15}$, —NH(C$_1$–C$_4$ alkylenylR$^{15}$), —SO$_2$R$^{15}$, —SO$_2$NR$^{15}$R$^{15}$, —NR$^{15}$C(O)OR$^{15}$, —NR$^{15}$C(O)R$^{15}$, optionally substituted cycloalkyl, optionally substituted 5–6 membered heterocyclyl, optionally substituted phenyl, lower alkyl substituted with R$^4$, cyano, nitro, lower alkenyl and lower alkynyl;

wherein $R^4$ and $R^{4b}$ are independently selected from H, $C_1$–$C_3$ alkyl, $C_2$–$C_3$ salkenyl, $C_2$–$C_3$ alkynyl, $C_3$–$C_6$ cycloalkyl, $C_4$–$C_6$ cycloalkenyl, phenyl, 5–6 membered beterocyclyl, halo, OF$_3$, SR$^5$, OR$^5$, OC(O)R$^5$, NR$^5$R$^5$, COOR$^5$, NO$_2$, CN, C(O)R$^5$, C(O)NR$^5$R$^5$, S(O)$_n$R$^5$, S(O)$_n$NR$^5$R$^5$, NR$^5$C(O)R$^5$, NR$^5$(COOR$^5$), NR$^5$S(O)$_n$R$^5$, OC(O)NR$^5$R$^5$, OS(O)$_n$NR$^5$R$^5$, NR$^5$S(O)$_n$OR$^5$, $C_1$–$C_6$ alkyl substituted with 1–3 substituents independently selected from optionally substituted phenyl and optionally substituted 5–6 membered heterocyclyl, and $C_2$–$C_6$ alkenyl substituted with 1–3 substituents independently selected from optionally substituted phenyl and optionally substituted 5–6 membered heterocyclyl;

wherein $R^5$ is selected from H, lower alkyl, phenyl and lower aralkyl;

wherein $R^{5b}$ is independently selected from H, $C_1$–$C_4$ alkyl, phenyl optionally substituted with $R^4$, and $C_1$–$C_4$ alkyl substituted with 1–3 substituents independently selected from $R^4$; and wherein $R^{15}$ is selected from H, lower alkyl, phenyl, 5–6 membered heterocyclyl, $C_3$–$C_6$ cycloalkyl, and lower haloalkyl; and wherein n is 0, 1 or 2;

or a pharmaceutically acceptable salt thereof.

6. Compound of claim 5 wherein Z is phenyl;

wherein $X^a$ together with the $R^{1a}$ group it is bound to is selected from

[Two chemical structures showing acyl groups with O, N-R$^{1a}$, R$^5$ substituents]

and wherein $R^z$ is $C_1$–$C_2$ alkylenyl, where one of the CH$_2$ groups may be substituted with O or —NH—;

wherein $R^{1a}$ is selected from phenyl, naphthyl, indenyl, tetrahydronaphthyl, 5–6 membered heteroaryl, and 9–10 membered fused heteroaryl;

wherein $R^{1a}$ is unsubstituted or substituted with one or more substituents independently selected from halo, —OR$^{15}$, —SR$^{15}$, —SO$_2$R$^{15}$, —CO$_2$R$^{15}$, —CONR$^{15}$R$^{15}$, —COR$^{15}$, —NR$^{15}$R$^{15}$, —NH(C$_1$–C$_2$ alkylenylR$^{15}$), —(C$_1$–C$_2$ alkylenyl)NR$^{15}$R$^{15}$, —SO$_2$NR$^{15}$R$^{15}$, —NR$^{15}$C(O)OR$^{15}$, —NR$^{15}$C(O)R$^{15}$, optionally substituted cycloalkyl, optionally substituted 5–6 membered heterocyclyl, optionally substituted phenyl, optionally substituted phenyl-$C_{1-2}$-alkylenyl, optionally substituted 5–6 membered heterocyclyl-$C_1$–$C_2$-alkyenyl, $C_{1-4}$-alkyl, cyano, $C_{1-2}$-hydroxyalkyl, nitro and $C_{1-2}$-haloalkyl;

wherein $R^4$ is selected from H, $C_1$–$C_3$ alkyl, $C_2$–$C_3$ alkenyl, $C_3$–$C_6$ cycloalkyl, phenyl, 5–6 membered heteroaryl, fluoro, chloro, CF$_3$, SR$^5$, OR$^5$, OC(O)R$^5$, NR$^5$R$^5$, COOR$^5$, NO$_2$, CN, C(O)R$^5$, C(O)NR$^5$R$^5$, SO$_2$R$^5$, SO$_2$NR$^5$R$^5$, NR$^5$SO$_2$R$^5$, and $C_1$–$C_6$ alkyl substituted with 1–3 substituents independently selected from optionally substituted phenyl and optionally substituted 5–6 membered heteroaryl;

wherein $R^{4b}$ is H;

wherein $R^5$ is selected from H, methyl and ethyl; and wherein $R^{5b}$ is independently selected from H, $C_1$–$C_2$ alkyl, phenyl optionally substituted with $R^4$, and methyl substituted with 1–3 substituents independently selected from phenyl, fluoro, chloro, CF$_3$, methoxy, acetyl, amino, methoxycarbonyl; and wherein $R^{15}$ is selected from H, $C_{1-2}$-alkyl, phenyl, $C_3$–$C_6$ cycloalkyl, and $C_{1-2}$-haloalkyl;

or a pharmaceutically acceptable salt thereof.

7. Compound of claim 6 wherein Z is

[Chemical structure of a meta-disubstituted phenyl ring]

;

wherein $X^a$ together with the $R^{1a}$ group it is bound to is

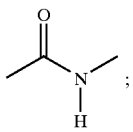

wherein $R^{1a}$ is selected from phenyl, thienyl, pyridyl, pyrimidinyl, pyridazinyl, pyrazolyl, imidazolyl, oxazolyl, thiazolyl, thiadiazolyl, furyl, pyrrolyl, indazolyl, indolyl, 2,1,3-benzothiadiazolyl, isoquinolyl, quinolyl, tetrahydroquinolyl, benzodioxanyl, and quinazolinyl;

wherein $R^{1a}$ is unsubstituted or substituted with one or more substituents selected from chloro, fluoro, bromo, methoxy, phenyloxy, benzyl, methylthio, methyl, ethyl, propyl, butyl, isopropyl, isobutyl, sec-butyl, tert-butyl, trifluoromethyl, difluoromethyl, pentafluoroethyl, hydroxymethyl, cyano, carboxy, aminocarbonyl, methylcarbonyl, amino, methylamino, cyclopropyl, cyclohexyl, piperidinyl, morpholinyl, N-methylpiperazinyl, N-ethylpiperazinyl, morpholinylmethyl, methylpiperdinylmethyl, methylpiperazinylmethyl, methylaminothiocarbonyl, N-methylamino-methylenyl, optionally substituted phenyl, N,N-diethylamino, and N,N-dimethylamino; wherein $R^{15}$ is selected from H, methyl, phenyl, cyclopropyl, cyclohexyl, and trifluoromethyl; wherein $R^4$ is selected from H, methyl, phenyl, fluoro, chloro, $CF_3$, methoxy, methoxymethyl, acetyl, amino, methoxycarbonyl and benzyl; and wherein $R^{5b}$ is H or methyl;

or a pharmaceutically acceptable salt thereof.

8. A pharmaceutical composition comprising a pharmaceutically-acceptable carrier and a compound of claim 1.

9. A method of treating breast cancer in a subject, said method comprising administering an effective amount of a compound of claim 1.

10. A method of treating angiogenesis in a subject, said method comprising administering an effective amount of a compound of claim 1.

11. A method of treating colon cancer in a subject, said method comprising administering an effective amount of a compound of claim 1.

12. A method of treating kidney cancer in a subject, said method comprising administering an effective amount of a compound of claim 1.

13. A compound of the Formula

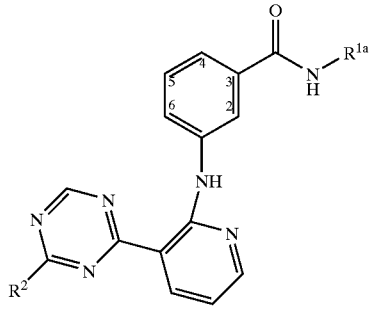

wherein $R^{1a}$ is phenyl, unsubstituted or substituted with one or more substituents selected from chloro, fluoro, bromo, methoxy, phenyloxy, benzyl, methylthio, methyl, ethyl, propyl, butyl, isopropyl, isobutyl, sec-butyl, tert-butyl, trifluoromethyl, difluoromethyl, pentafluoroethyl, hydroxymethyl, cyano, carboxy, aminocarbonyl, methylcarbonyl, amino, methylamino, cyclopropyl, cyclohexyl, piperidinyl, morpholinyl, N-methylpiperazinyl, N-ethylpiperazinyl, morpholinylmethyl, methylpiperdinylmethyl, methylpiperazinylmethyl, methylaminothiocarbonyl, N-methylamino-methylenyl, optionally substituted phenyl, N,N-diethylamino, and N,N-dimethylamino;

wherein $R^2$ is —$NHR^{5b}$.

wherein $R^{5b}$ is independently selected from H, phenyl substituted with one to three methoxy substituents;

or a pharmaceutically acceptable salt thereof.

14. A compound of the Formula

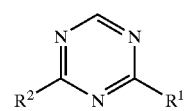

wherein $R^1$ is

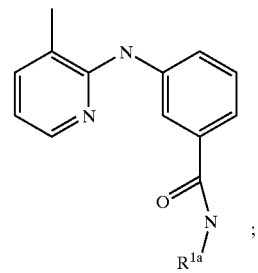

wherein $R^{1a}$ is selected from unsubstituted or substituted aryl, 5–6-membered heteroaryl and 9–10 membered fused heteroaryl, wherein $R^{1a}$ is substituted with one or more substituents independently selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5–6 membered heterocyclyl-$C_1$–$C_2$-alkylenyl, optionally substituted heteroaryl, optionally substituted heteroaryloxy, $C_{1-6}$-haloalkyl, and $C_{1-6}$-alkoxy;

wherein $R^2$ is selected from fluoro, chloro, bromo, $NHR^5$ and methyl optionally substituted with 1 to 3 substituents independently selected from phenyl, $R^9$, chloro, fluoro, $OR^5$, $OC(O)R^5$, $NR^5R^5$ and $COOR^5$;

wherein $R^4$ is selected from $C_1$–$C_4$ alkyl, optionally substituted phenyl, chloro, fluoro, hydroxy, methoxy and benzyl;

wherein $R^5$ is independently selected from H, $C_1$–$C_4$ alkyl, $C_2$–$C_4$ alkenyl, $C_2$–$C_4$ alkynyl, $C_3$–$C_6$ cycloalkyl, $C_4$–$C_6$ cycloalkenyl, $R^9$, phenyl optionally substituted with $R^4$, and $C_1$–$C_4$ alkyl substituted with 1–3 substituents independently selected from aryl, $R^7$ and $R^9$ groups; and wherein $R^9$ is selected from 5–6-membered heteroaryl, and wherein 0, 1, 2 or 3 atoms of each ring may be substituted by a substituent independently selected from $C_1$–$C_4$ alkyl, fluoro, chloro, trifluoromethyl, optionally substituted phenyl, hydroxy, methoxy, amino, methylamino, carboxy, methoxycarbonyl, formyl, methylcarbonyl, acetyl, and aminocarbonyl;

or a pharmaceutically acceptable salt thereof.

* * * * *